US005851780A

United States Patent [19]
Chiang

[11] Patent Number: 5,851,780
[45] Date of Patent: Dec. 22, 1998

[54] GENOMIC DNA OF HUMAN CHOLESTEROL 7α-HYDROXYLASE AND METHODS FOR USING IT

[75] Inventor: John Young Ling Chiang, Stow, Ohio

[73] Assignee: Northeastern Ohio University, Rootstown, Ohio

[21] Appl. No.: 477,952

[22] Filed: Jun. 7, 1995

Related U.S. Application Data

[63] Continuation of Ser. No. 361,458, Dec. 21, 1994, which is a continuation of Ser. No. 135,488, Oct. 13, 1993, abandoned.

[51] Int. Cl.$^6$ ....................................... C12Q 1/26
[52] U.S. Cl. ............................................ 435/7.6; 435/184
[58] Field of Search ...................................... 435/7.6, 189

[56] References Cited

PUBLICATIONS

Karam, W. G. et al., "Polymorphisms of Human Cholesterol 7α–Hydroxylase", *Biochem. and Biophys. Res. Comm.* 185(2): 588–595 (1992).
Breslow, J. L. et al., "Transgenic Mouse Models of Lipoprotein Metabolism and Atherosclerosis", *Proc. Natl. Acad. Sci. USA* 90: 8314–8318 (1993).
Cohen, J. C. et al., "Cloning of the Human Cholesterol 7α–Hydroxylase Gene (CYP7) and Localization to Chromosome 8q11–q12", *Genomics* 14: 153–161 (1992).
Nishimoto, M. et al., "Structure of the Gene Encoding Human Liver Cholesterol 7α–Hydroxylase", *Biochimica. et Biophysica. Acta.* 1172: 147–150 (1992).
Thompson, J. F. et al., "Cholesterol 7α–Hydroxylase Promoter Separated from Cyclophilin Pseudogene by Alu Sequence", *Biochimica et Biophysica Acta* 1168: 239–242 (1993).
Li, Y. C. et al., "The Expression of a Catalytically Active Cholesterol 7α–Hydroxylase Cytochrome P450 in *Escherichia coli*", *The Journal of Biological Chemistry* 266(29): 19186–19191 (1991).
Molowa, D. T. et al., "Transcriptional Regulation of the Human Cholesterol 7α–Hydroxylase Gene", *Biochemistry* 31: 2539–2544 (1992).
Nishimoto, M. et al., "Structural Analysis of the Gene Encoding Rat Cholesterol α–Hydroxylase, The Key Enzyme for Bile . . . ", *The Journal of Biological Chemistry* 266(10): 6467–6471 (1991).
Jelinek, D. F. et al., "Structure of the Rat Gene Encoding Cholesterol 7α–Hydroxylase", *Biochemistry* 29(34): 7781–7785 (1990).
Chiang, J. Y. L. et al., "Cloning and 5'–Flanking Sequence of a Rat Cholesterol 7α–Hydroxylase", *Biochimica et Biophysica Acta* 1132: 337–339 (1992).
Lusis, Aldons J., "The Mouse Model for Atherosclerosis", *TCM* 3(4): 135–143 (1993).
Dueland, Svein et al., "Effect of Dietary Cholesterol and Taurocholate on Cholesterol 7α–Hydroxylase and Hepatic LDL Receptors in Inbred Mice", *Journal of Lipid Research* 34: 923–931 (1993).
Dueland, Svein et al., "Expression of 7α–Hydroxylase in Non–hepatic Cell Results in Liver Phenotypic Resistance of the Low Density Lipoprotein Receptor to Cholesterol Repression", *J. Bio. Chem.* 267(32): 22695–22698 (1992).
Ness et al., "Effect of Thyroid Hormone on Hepatic Cholesterol 7α–Hydroxylase, LDL Receptor, HMG–CoA Reductase, Farnesyl Pyrophosphate Synthetase and Apolipoproteein A–I mRNA Levels in Hypophghysectomized Rats", *Biochem. Biophys. Res. Comm.* 172(3): 1150–1156 (1990).
G. Ciliberto et al., *EMBOJ* 6: 4017–4022 (1987).
J.W. Gordon et al., *Science* 214: 1244–1246 (1981).
R.L. Brinster et al., *Proc. Natl. Acad. Sci. USA* 85: 836–840 (1988).
Abstract of M. Noshiro et al., "Molecular cloning and sequence analysis of cDNA encoding human cholesterol 7α–hydroxylase", *FEBS Lett.* 268(1): 137–140 (1990).
Sambrook et al., *Molecular Cloning: A Laboratory Manual*, 2nd Edition, Cold Spring Harbor Laboratory Press, 16.1–16.72 and 17.1–17.41 (1989).
M. Ramirez et al., "Cholesterol and Bile Acids Regulate Cholesterol 7α–Hydroxylase Expression at the Transcriptional Level in Culture and in Transgenic Mice", *Mol. Cell. Biol.* 14(4): 2809–2821 (1994).

*Primary Examiner*—Charles L. Patterson, Jr.
*Attorney, Agent, or Firm*—Foley & Lardner

[57] ABSTRACT

Genomic DNA of cholesterol 7α-hydroxylase and a minigene are disclosed. The minigene is used for making a transgenic animal that produces functionally active cholesterol 7α-hydroxylase and functions as a disease model. A cholesterol 7α-hydroxylase promoter region and reporter gene construct is provided, as well as a transgenic animal that expresses the promoter/reporter gene.

3 Claims, 18 Drawing Sheets

FIG. 3

```
  1 MMTTSLIWGIAIAACCCLWLILGIRRRQTG
 31 EPPLENGLIPYLGCALQFGANPLEFLRANQ
 61 RKHGHVFTCKLMGKYVHFITNPLSYHKVLC
 91 HGKYFDWKKFHFATSAKAFGHRSIDPMDGN
121 TTENINDTFIKTLQGHALNSLTESMMENLQ
151 RIMRPPVSSNSKTAAWVTEGMYSFCYRVMP
181 EAGYLTIFGRDLTRRDTQKAHILNNLDNFK
211 QFDKVFPPALVAGLPIHMFRTAHNAREKLA E
241 SLRHENLQKRESISELISLRMFLNDTLSTF
271 DDLEKARTHLVVLWASQANTIPATFWSLFQ
301 MIRNPEAMKAATEEVKRTLENAGQKVSLEG
331 NPICLSQAELNDLPVLDSHIKESLRLSSAS
361 LNIRTAKEDFTLHLEDGSYNIRKDDIHALY
391 PQLMHLDPBIYPDPLTFKYDRYLDENGKTK
421 TTFYCNGLKLKYYYMPFGSGATICPGRLFA
451 IHEIKQFLIMLSYFELELIEGQAKCPPLD
481 QSRAGLGILPPLNDIEPKYKFKHL*
```

FIG. 4A

```
  1 TTTTTGGTTA TCTTTTCAGC CGTGCCCCAC TCTACTGGTA CCAGTTTACT GTATTAGTCG
 61 ATTTTCATGC TGCTGATAAA GACATACCTG AAACTGGACA ATTACAAAA  GAAAGAGGTT
121 TATTGGACTT ACAATTCTAC ATCACTTGGG AGGCCTCACA ATCATGATGG AAGGAGAAAG
181 GCACATCTCA CATGGCAGCA GACAAGAAAA GAGCTTGTGC AGGGAAACTC CTCTTTTTAA
241 AACCATCAGA TCTCATGAAA TTTATTCATT ATCATGACAA TAGCACAGGA AAGAACTGCA
301 CCCATAATTC AGTCACCTCC TACCAGGTTC CTCCCACAAC ACGTGAGAAT TCAAGATGAG
361 ATTTGGATGG GGACACAGCC AAACCATGTC ACACTACCAT GCCTGACTTC CTTTCCATTT
421 TTGTATATTT GCTTGTTCTT CATTTGCCCG AGAAGTAACT CTAAAGGGCT GTATTATTTG
481 GATATTAGAT TGGCATTTTA TCTGACTGGG ATATCTTGCT GTGATTGTCC ATGTATAAGA
541 TCAGCTTTTC TATAAGCCAT ATTTTTAAAA AGATATATTA ATTTTTTAAA AATCCACCTG
601 TCTAAATAAA TGCACAAAGC CCCCAAAAA  CCTAGATTCT AAGAAAAATC TATGTACTGC
661 CATACAATGA TTGATATTAA TATTATGGT  GATAAATTAC ACACAAAAAA TGTGTGATCT
721 CTGTTTAAAC AGGCAAAAAC AAAAACACA  TGAAATAAAT CTATGGCATC TATAGCCAAA
781 ACTGGAAACA ACCCACATAT CCATCAATAG GAAATCAGTT AAATAAATTA TAGTACATTT
841 ATCCAATGGA AGATTAAGCA CATATTCAAT ATAATTATTT ATACACACAT ATAGATACAC
```

FIG. 4B

```
 901 ACATGTATAA ATATAGAGAA TACTGTGGGT GTATGTGTGT GTGTGTTTAT ATACATATAT
 961 ATACACACAC AGTACTGTTG CCTACCTTCT TTTGTCTTAA TTCTGTGAAC TCTCATTCAC
1021 TCTGCTTCAG TAGGATACCT CCTTCTTTTT GGTTCTTAGA CTCACCAAGT TGATCCTTGA
1081 CTCAAGACAT TGCATTTGCT GCTTCCTCTT CCTGGAATAT CCTTCCTTCT GATATTCACA
1141 TGAGTAGTCT CTTCTTGTCA TTCAGATCTC AAATGTCACA ATTTCAGAGA GCCCATCTCT
1201 GATCATCATA TCTAAAGTTG TCCTCATTCC CCCATAGCTT TCTATACCAT GTTTTATTTT
1261 TTTCATAACA TGTATTTTAT TACTCCTTTC TCCATTGGAA TAGAATCTCC ATTAGATTAG
1321 GAAATCTGCC TATCTTATTA ATGCCTGCCA CTGGAATACT TTTGAAGAGT TCTTGGCACG
1381 TAATAAATAC TCAACTAATA TTTTTGTGTA CACAGAAATA AAGTTTGGAA GAACAGATGC
1441 CAAATTGTTA CTAGTGGTTA CTTCTGAGTA AAGGAGTAGC ATGGTAGGTA AATTATTAAT
1501 AGATGTTCAC TTTCCACCAA GATATGTTTT AGTTAGTCTT AACTTACTTG AAATGAAATT
1561 TATTACTTTA ATAATTAGAA ACATTTTAGT CACAAGAATG ATAGATAAAA
1621 TTTTGATGCT TCCAATAAGT TAGAGGATGC ACTTATGTAG AATACTCTCT
1681 TGAGGATGTT AGTGAGTAA CATGTTACTA TATGTAGTAA AATATCTATG ATTTTATAAA
```

FIG. 4C

```
1741 AGCACTGAAA CATGAAGCAG CAGAAATGTT TTTCCCAGTT CTCTTTCCTC TGAACTTGAT
1801 CACCGTCTCT CTGGCAAAGC ACCTAAATTA ATTCTTCTTT AAAAGTTAAC AAGACCAAAT
1861 TATAAGCTTG ATGAATAACT CATTCTTATC TTTCTTTAAA TGATTATAGT TTATGTATTT
1921 ATTAGCTATG CCCATCTTAA ACAGGTTTAT TTGTTCTTTT TACACATACC AAACTCTTAA
1981 TATTAGCTGT TGTCCCCAGG TCCGAATGTT AAGTCAACAT ATATTTGAGA GACCTTCAAC
2041 TTATCAAGTA TTGCAGGTCT CTGATTGCTT TGGAACCACT TCTGATACCT GTGGACTTAG
2101 TTCAAGGCCA GTTACTACCA CTTTTTTTT TCTAATAGAA TGAACAAATG GCTAATTGTT
2161 TGCTTTGTCA ACCAAGCTCA AGTTAATGA TCTGGATACT ATGTATATAA AAAGCCTAGC
2221 TTGAGTCTCT TTTCAGTGGC ATCCTTCCCT TTCTAATCAG AGATTTTCTT CCTCAGAGAT
2281 TTTGGCCTAG ATTTGCAAAA TGATGACCAC ATCTTTGATT TGGGGATTG CTATAGCAGC
2341 ATGCTGTTGT CTATGCTTA TTCTTGGAAT TAGGAGAAGG TAAGTAATGT TTTATCTTTA
2401 AATTGCTCTT TGATTCATCC ATTTAATTTT TTTACCTTCA TTTTTATACA GTAAATTTGG
2461 TTTTCTATAT TTACACATAT TAGCATTATC TTCCTTATGT TTTAAATGAA AAATTTGATT
2521 TGAATTTTA AAGTAATATC TTTTTTACTA TATCTCACAA GACATATGAC AGCTTCCCTT
```

FIG. 4D

```
2581 TTTAGTATTG GCATATACCG ATGGTAATAT ATAAATGTAT ATTGGTGTTA AACATAACTG
2641 ACAGAAATTG TATAAGGTCT CTATGTACAT TTATATGTGT ATCTAAAGAG GAAGCCAAGA
2701 TTAGTAAGGA TACAAGTAGC AAGTGGGAAT CTACAATGGA AAGGATTGCT TTCTCTCACA
2761 TGGCTTCAAT AGATACTCTT GCTTAAATAA ATGTTCTCTT TTAAGCTCAT TCTTGTGCAT
2821 CGCATAGACT CAGCCCTAAGC CTGAACAAGA GCATAGAGCC TGAGCTGATC ATTCTATTAC
2881 TGTTTTAAA TAAATGTTAA TCAACTGTGG TGAATTGGGA AAGTTTGCTG AGTGTATGTG
2941 ACATCGATTT CATTTATTTA TAGTTTATTT AAGAATGCAA GAAAAACAAA TACAGTCAGA
3001 TCCAGAACCA TAGTTTATTT AACTTCTAAT TGGCTCAAGG AGTAATTGTG GGGAGGCATA
3061 TAGATATTCT CTGCTATGTC AATCTCAAAA AGAGAAAATA ACCCTAACCA TCTTTCAGCT
3121 TTGTAGATTG CTATGTGTTT TCTGCCTTTG CAGTTTCTTT CAGGCCTGAT AGTTTTTACT
3181 TTTAATTAAA CTACTTATCT TCAAACTAAG AAAAGAAAGG TAATTACTTT ATACTGTATT
3241 ATTCTATCAA GAGGTACAGA AGTTTATGTT GGAAAATAAG TTTACATGTT CTAATAAAAA
3301 CATTTAAAG GAGCACTGAA TTACAATAGA TGATTCCGTC AGTGTTTATC TTACTCAATT
3361 TCATTTATA ATAAGCTGAT TTCTCACATG AGATTCTTCT TCTCTGAAAC CATCCTTATA
3421 GAATATAATA TAGATATCTT TAAACTAGGA ATATTTTCAA AACCTCAGTT CTGAAATCCT
```

FIG. 4E

```
3481 CCCTTATTCA GTGATCTGTG TCTTTAAAGA AAATAATCAA AAGAAACATT TTGAGATATT
3541 TAGAAAAATG ATGCTTAGCA AAGTGATAAA CACTAGAATG TAGTTTTGTT TCCGCACTGA
3601 CAACAAGAAT CTTGTTGGTC TTGTAAATCC TTTTGCCTGT ATCACTGGGA AAAGTGATGA
3661 GCACATAGTA GACGGGTGCT TGTTGAATGT GTATATGGAC GGATGCATGA ATGGATGGAT
3721 TTAGTAATCC TTTCCACCAA CATATCATGT TACTAGGTTA ATATAACCTA TTACTGTAGT
3781 AAAAGAGCAG GGCCCATCCA ACAAAAGAAA TATCTATAAA CTATAGGGTT TCAAAGTTTG
3841 AAGTCAGTGG GAAAATTTT AAAACCTGAT GTAAGTAAAA ACCCAAAACT GTAATCATCC
3901 ATGTCTATCA TACACTTGTG TCTGACAGGC AAACGGGTGA ACCACCTCTA GAGAATGGAT
3961 TAATTCCATA CCTGGCTGT GCTCTGCAAT TGGTGCCAA TCCTCTTGAG TTCCTCAGAG
4021 CAAATCAAAG GAAACATGGT CATGTTTTTA CCTGCAAACT AATGGAAAA TATGTCCATT
4081 TCATCACAAA TCCCTTGTCA TACCATAAGG TGTTGTGCCA CGGAAAATAT TTTGATTGGA
4141 AAAAATTTCA CTTTGCTACT TCTGCGAAGG TAAGCAGTTT TACATTTATA TACCATTCTG
4201 TTTGTCTTCT ACCTTTTTAT GTGCTTGTCT ATTTAGAAAT TTTGATGTAC TTAGATTTTA
4261 TGATAAAGGT GTTGAAGAGA GTTATCCTTA TGTGGAGATT CTTAGAAACA TAAATAAATT
4321 ATACGTAGCT TCTTAGTAAT AATCATTTAG AAAGTCAAAA TAGGTATAGA TTTCCGTCAT
4381 TTGCTTTGCA CGAGCTAATG AGGGTGAAAT ACAGATTAAA TGCTCTACTG AGACAGGTGG
4441 CACTGTACGA ATAAGATAGA TTAAAATTCA TCACATCAGC AATGTCTATG CAGAGCGAAG
4501 TGACGGAAAC CTAACATTCA GCAGTTGTCT CACCACACTT GTGCCACACA GTGTTTCATT
```

FIG. 4F

```
4561 TTGATAAGGA ATTGGCAAGA TATTTTAACA TCATTTAGAT GTAATAAAG AAGATCGTT
4621 ACTGAGAAAA AAAACCAATA ACTACTTACT TACTGCAAAT AAATATTAGC TTTGGTCTTT
4681 GTGACTAAGT AGCTTAAAGT TTGGTTAAAA TACATCTACA GCTGGACACA ATGAAACACA
4741 CCTGTAGTCC CTGCTATTTG AGAGGCTGAG GCAGGAGGAT CGCTTGAGTC CAGGAGTTTG
4801 AGGCTGCAGT GAGCTATCAT TGTGTCACTG CACTCCAGCC TGGGTGACAA TGTGAGACCC
4861 CATCTCTAAA AGAAAAGAA AAAGAAATCT ACAAATAATA TAAAAGATAA CTAATGATTT
4921 TAAAACATTA TCAATTAGTT TATGTGCAAT AGCTGTAAAT AAGTGCAGTA GCATAAGAAA
4981 TAAGACATAG ATGACTTGAG TGATCCAGGG GAGTGCCACT GAAGTTGGCT TTAAAGGAAA
5041 GGTACAGTTT GGTCATTTAT TTGTAAAGTG CTATGAACTT GTACAAGGA AAGCCAATTT
5101 CCCGTGTTTA CCAAGTAAGG AACTATGAAA GTATCTAATC CGTTTTTCAG TCATTTACTA
5161 TGACTAGGTC AGGTTTAACT TCTTTTTCTG CATGTTTTAT TTGCTATCAG GCATTTGGGC
5221 ACAGAAGCAT TGACCCGATG GATGAAAATA CCACTGAAAA CATAAACGAC ACTTTCATCA
5281 AAACCCTGCA GGGCCATGCC TTGAATTCCC TCACGGAAAG CATGATGAA AACCTCGAC
5341 GTATCATGAG ACCTCCAGTC TCCTCTAACT CAAAGACCGC TGCCTGGGTG ACAGAAGGGA
5401 TGTATTCTTT CTGCTACCGA GTGATGTTTG AAGCTGGGTA TTTAACTATC TTTGGCAGAG
5461 ATCTTACAAG GCGGACACA CAGAAAGCAC ATATTCTAAA CAATCTTGAC AACTTCAAGC
5521 AATTCGACAA AGTCTTT
```

FIG. 5A

```
   1 GAATTCTACT CTTTAAAGGG GTGAATATTA TGGTACTTGA ATTTATCTC AAGAAAATG
  61 AATAAAAAGT AACTAAATCA TTGAAAATAT CTGATGGCAT GGGTTTGTG GGGTAACTGG
 121 CATTCCACAG TGATTTTCAA AGGGCTTGTG CTGTTTTCAT TTTGCTTTGT TTTAGTTATG
 181 GAGCCCTTCC TTGAAACAAA CTTCATACTA CAGTCCTCTT TCATGAAGCA GAAGAGGCA
 241 GTGGGCAGAG CTCTCCTTTG GCTTTCTCCC CCACCACAAC AGGGAGCCCT GGAGCTCTAG
 301 GAGAGAAAAT CTGAAATATA AGGGCATGC ATGTGAGCTG TGGAGTCCCA GAGCCCTGGG
 361 TTTGCATCCT AGATCTGCAA CTCCCGTGAA TTGAGTTTTG GGAAGTTGCT GAAACTCTGA
 421 CCTCCTGTTT TCTCATGGTA TTGTTGTAAG GGTTAAATGA GACAATGTAT GTGAAGACCC
 481 TGGCCCACA GTAGAGGCTC TGCACACATT TCAGCGATAC TTTCCTCATG TATTTCCAAA
 541 AATGTTTCT CATTTTCTTA AAATGTCAGA AAGAAGACAA CAGAACTTAC TTGCCTTTA
 601 CAACAGAACA AATGGAGCAA GTCAGAGGTC AAGGTGCTAA CATTCTTCAT GGTTCCTCAC
 661 CACCTTTTGT TCTGTTAGCC TATAGGGAAA AGTCTTCTTT CTCATCTCAT TATCTGCAGG
 721 GGAAAATAGT ACTTCAGCAA GTGATCCAGT TGAAGAACAT CTCCAGGGCC ATTAACATAC
 781 AGAGGTTTGT TCTACTCTCT CTGTGCTCCA TGTCTAAGAA CCTCAGCCTT CCTCCTAGGA
 841 GCTAGGGAAA GTCAGGAAAG TGAAAATAGT ACCCCAGCTA ATGAACTGCC CTGTGCTGGC
 901 CTGAGAAGAC AAGACCAGCT TCCTCAATGG CTCAAGATTT GGTTTCCTTC AATATGTCCT
 961 TTTGGAAATA TGTCCATGAC ATCGGAGAGA TAAAAGGAGC CAGGATTGCT CACATTCAGG
1021 AAAAAAGCTC CACTATCTTT CTCTCTCTCC CTCTTTTCTCT CCCTCCCCCT GACTGCCCTC
1081 TTCTCTATCT CTCCTCTCTC CTGAGCTGGC AAGTTCAAT GGTCGCAGAA AGCCGAAGAA
1141 ACAAGTGGGC CTCCTGGAAC AAAGTTCAAA AGCCCGAAAA CGGAAGAAA ACTAACACA
1201 AAAGTAAAGG AACCACTTAG CCTTCTTTGA TTCCAGCCCC CCAAGCCTGT CTTTAACTTG
```

FIG. 5B

```
1261 GATGAATGGA GTTCTTCCTG TGCTACAGCA CCGCATAGTA GGGGCTGCCC TGGGCCTGAA
1321 GCCAGAGCTT CACCATATTC AGTCATCTGT ACATTGAGGC AACAGTGCCT GCTTCATGT
1381 GCTACCCTGT GGATTAAATG AAGCAAGTTT TTGATGATCT TGACACTGAA TATTGATGCA
1441 TTGGTCAGAC TTTTTCTGAT AGTAAAAAAT GGTGGTTTCT TGTTGTCAGA AATCAAATCA
1501 ATATATTTGT TCTCCTGTTG ATTAGCTATG TCCCCTAGAG GGCAGCGACT TTGCCTGTCT
1561 TATTTATCTC TGCATCTCCA GCACTTAAAA GGTGCCTTGC ATAAGGTACA TATTAAGTTC
1621 ATATGAATGA ATGAATGAAA TGCATATGAT TTATTCATAC CCAGTTGGTG GTGTGTTTAC
1681 CCTTTCCTAA ACCTGTAGTC AGATGCCCTT TGAATCCCCT GTACTTCTTG TGAGGTACTG
1741 TGCTGTAAAG GTGGACTATC ACACTTCAGT TCAGAGCAAT CTGGGCTTGA ATCCTGGATT
1801 TGCCAGTTTA TTAACTATAG CAAACATTTT TGAGCATACA TTGTGCCAAG TGCTAGGCTA
1861 ACTGTCTTAC ACACATTGTC TTATTTGTC TTAATATCTA TGAGTCATGC ACTATAATCA
1921 TCCCCATTTT ACAGATAAGA AAGCAAAGAC TTGGAGAGAA AAAGCATCTT GTTCAAAGGT
1981 AAATACTTAA TGGCCAAGCC AACATGCAAA TCTAGATTTA ATTGCAGCTT CCTCTTGATC
2041 TACCATTCGA ACTAATTCAA GCTATACCTG ATTTCCCACT GAACCTTCTT GCCTCTACTT
2101 CCTCATCTTT AACATGGTCA AAATACCTGT CCTGCCCAAG TTAGTTATTT CATTAAAGTA
2161 GAAAAATACA AGAGAAGCTT TTAAAATGTG AAACCTCAAA TGAATGTAAA ATTATGATGA
2221 TTCCTTTAGA ATTTGTCAAC ACCTTCTTTT CTCTACTCCT GCTAGGCATT TACAATCTCA
2281 AAACCATGTA TTTAAGATGC AAAACTATAT TTGTATTTGC CATAACTCGT TTCTTTCCTT
2341 ATGGCTTCAT GAAAATGTGG CTCGAATGTG TTTATTATGA AAGCCCCAAA TTAATCACGA
2401 CAAGACTTCA CCAGCCCATT CCACAATACA CTCCACATAGA TTTGCCCTGA CTTAGAAAAC
2461 TCATATACAG TCTTGATTCA GTACAGCTCT GTGATGCTCT TGGAAAATGC AAAGTGCTTT
2521 CTTAATTGAG GCAATCTGTG TCCCACTACA GAGAGGTGGT TTAACTGTGT AATTC
```

FIG. 6A

```
   1 AGAGCAACCT GGGCAACATA GCAAACCCT GTCTCTGCAA ACAATAAAA GAAGAAATT
  61 AGCTGGGTAT GGTGGCACAT GCTATAGTCG CAGCTACTCG AGAGGTTGAG GTGGAGGAT
 121 CAGTTCAGCC TGGGAGGTTG AGGCTGCAGT GAGCCAGATC ATGCCACTGC ACTGCAGCAT
 181 GGGCAACAGA ATGAGACCCT GGCTAAAAGA AAACAAAATA AAAAATTCAG ACACAGGTTG
 241 AATCATTGAT AACAGCATAG TGGTAACAGA AGAAAAGTTT GGGAAATTTT TATCTGATCA
 301 GCTTCCCATA CCCTGTTCAT CTTTGTGTTA TGCACTGCCA GGCTGTCTGT AGGTTCAGAC
 361 TCTATATCAT ATGACCTTCA AACACTTGGT TTGTTCTTCT CCTTCCTTCC TCCCTCTTC
 421 TTTCATTTTT TATCTTTTTT TCTTTTAAAA TGTTTAGATA GTATAATAAG GAACTGCTGA
 481 GGCTTTCCAG TGCCTCCCTC AACATCCGGA CAGCTAAGGA GGATTTCACT TTGCACCTTG
 541 AGGACGGTTC CTACACATC CGAAAAGATG ACATCATAGC TCTTTACCCA CAGTTAATGC
 601 ACTTAGATCC AGAAATCTAC CCAGACCCTT TGGTAAAGTC GCAGTGTGCC CGAATTGAAA
 661 TTCAATATCC AGGTGATAGC TACCTAGATC TAAATAAAGA GGAAATTTAC AATGGTAGAA
 721 TTGATTTCT CATAGTAGTC ACAGGAATTG TCTGACTTAA TTGTGTTAAA TATTCATATA
 781 TTTTGGAAAA TTTAGATAGT GGTCTGAATT TTTCATTTTA GTCCTGATAT TTGCCATCAC
 841 ACAGTCTTTG CTAGATTATA TTTGCAGTCA TGATAATAAA CCTGCCACTT TTTTTTCTT
 901 AAAAGCACC TCCTCCCAAA TCCAGGAAAT TGGAGGCTAA TATATTGATT ATTCTAGTTT
 961 CTTCTGGGAA CCCTTCTCTC TCTAGCTCTG CCTGACTAAG GAACTAATCG TTCAAGCAGG
1021 ATAGGAAGGT ATCACAAGC TTCCTTAGCT GCATTAAGCT CCTGTTCCTT ATTACTTTCT
1081 GATTCAATGT GGAGTATTTG CTAAATCACT AATGGGGTAG TATATTGATT AAATTACTTC
1141 TTTGGAGCTT CCAGTTTAG AAAGAGATAA ATTTCTTTAA AACTAGCTTA AAGGCGGTTT
```

FIG. 6B

```
1201 TCTTTGTATT TTTATTGCAG ACTTTTAAAT ATGATAGTTA TCTTGATGAA AACGGAAGA
1261 CAAAGACTAC CTTCTATTGT AATGACTCA AGTTAAAGTA TTACTACATG CCCTTTGAT
1321 CGGGAGCTAC AATATGTCCT GGAAGATTGT TCGCTATCCA CGAAATCAAG CAATTTTGA
1381 TTCTGATGCT TTCTTATTTT GAATTGGAGC TTATAGAGGG CCAAGCTAAA TGTCCACTTT
1441 TGGACCAGTC CCGGGCAGGC TTGGGCATTT TGCCGCCATT GAATGATATT GAATTTAAT
1501 ATAAATTCAA GCATTGTGA ATACATGGCT GGAATAAGAG GACACTAGAT ATTACAGAC
1561 TGCAGAAACAC CCTCACCACA CAGTCCCTTT GGACAAATGC ATTTAGTGGT GGCACCACAC
1621 AGTCCCTTTG GACAAATGCA TTTAGTGGTG GTAGAAATGA ATTTAGTGGT CCAATGTTGT
1681 TCACCAGTGC TTGCTGTGA AATCTTAACA TTTTGGTGAC GTAGAAATGA TGCTATCACA
1741 GACTCTGCTA GTGAAAAGAA CTAGTTTCTA GGAGCACAAT AGTTTCCAGA CATTGTATA
1801 AGTCCATGAA TGTTCATATA GCCAGGGATT GAAGTTTATT ATTTTCAAAG GAAAACACCT
1861 TTATTTATT TTTTTTCAAA ATGAAGATAC ACATTACAGC CAGGTGTGGT AGCAGGCACC
1921 TGTAGTCTTA GCTACTCGAG AGGCCAAAGA AGGAGGATGC TTGAGCCCAG GAGTTCAAGA
1981 CCAGCCTGGA CAGCTTAGTG AGATCCCGTC TCCAAAGAAA AGATATGTAT TCTAATTGGC
2041 AGATTGTTTT TTCCTAAGGA AACTGCTTTA TTTTTATAAA ACTGCCTGAC AATTATGAAA
2101 AAATGTTCAA ATTCACGTTC TAGTGAAACT GCATTATTTG TTGACTAGAT GGTGGGGTTC
2161 TTCGGGTGTG ATCATATATC ATAAAGGATA TTTCAAATGT TATGATTAGT TATGTCTTTT
2221 AATAAAAAGG AAATATTTTT CAACTTCTTC TATATCCAAA ATTCAGGCT TTAAACATGA
2281 TTATCTTGAT TTCCCAAAAA CACTAAAGT GGTTTT
```

FIG. 8

```
   1 AGTTTAACTT TAGTAAGGAG TCTAGACCAT GGCCAGGAGA AGGCAAACGG GTGAACCACC
  61 TCTAGAGAAT GGATTAATTC CATACCTGGG CTGTGCTCTG CAATTTGGTG CCAATCCTCT
 121 TGAGTTCCTC AGAGCAAATC AAAGGAAACA TGGTCATGTT TTTACCTGCA AACTAATGGG
 181 AAAATATGTC CATTTCATCA CAAATCCCTT GTCATACCAT AAGGTGTTGT GCCACGGAAA
 241 ATATTTTGAT TGGAAAAAAT TTCACTTTGC TACTTCTGCG AAGGCATTTG GGCACAGAAG
 301 CATTGACCCG ATGGATGGAA ATACCACTGA AAACATAAAC GACACTTTCA TCAAAACCCT
 361 GCAGGGCCAT GCCTTGAATT CCCTCACGGA AAGCATGATG GAAAACCTCC AACGTATCAT
 421 GAGACCTCCA GTCTCCTCTA ACTCAAAGAC CGCTGCCTGG GTGACAGAAG GGATGTATTC
 481 TTTCTGCTAC CGAGTGATGT TTGAAGCTGG GTATTTAACT ATCTTTGGCA GAGATCTTAC
 541 AAGGCGGGAC ACACAGAAAG CACATATTCT AAACAATCTT GACAACTTCA AGCAATTCGA
 601 CAAAGTCTTT CCAGCCCTGG TAGCAGGCCT CCCCATTCAC ATGTTCAGGA CTGCGCACAA
 661 TGCCCGGGAG AAACTGGCAG AGAGCTTGAG GCACGAGAAC CTCCAAAAGA GGGAAAGCAT
 721 CTCAGAACTG ATCAGCCTGC GCATGTTTCT CAATGACACT TTGTCCACCT TTGATGATCT
 781 GGAGAAGGCC AAGACACACC TCGTGGTCCT CTGGGCATCG CAAGCAAACA CCATTCCAGC
 841 GACTTTCTGG AGTTTATTTC AAATGATTAG GAACCCAGAA GCAATGAAAG CAGCTACTGA
 901 AGAAGTGAAA AGAACATTAG AGAATGCTGG TCAAAAAGTC AGCTTGGAAG GCAATCCTAT
 961 TTGTTTGAGT CAAGCAGAAC TGAATGACCT GCCAGTATTA GATAGTATAA TCAAGGAATC
1021 GCTGAGGCTT TCCAGTGCCT CCCTCAACAT CCGGACAGCT AAGGAGGATT TCACTTTGCA
1081 CCTTGAGGAC GGTTCCTACA ACATCCGAAA AGATGACATC ATAGCTCTTT ACCCACAGTT
1141 AATGCACTTA GATCCAGAAA TCTACCCAGA CCCTTTGACT TTTAAATATG ATAGGTATCT
1201 TGATGAAAAC GGGAAGACAA AGACTACCTT CTATTGTAAT GGACTCAAGT TAAAGTATTA
1261 CTACATGCCC TTTGGATCGG GAGCTACAAT ATGTCCTGGA AGATTGTTCG CTATCCACGA
1321 AATCAAGCAA TTTTTGATTC TGATGCTTTC TTATTTTGAA TTGGAGCTTA TAGAGGGCCA
1381 AGCTAAATGT CCACCTTTGG ACCAGTCCCG GGCAGGCTTG GGCATTTTGC CGCCATTGAA
1441 TGATATTGAA TTTAAATATA AATTCAAGCA TTTGTGAATA CATGGCTGGA ATAAGAGGAC
1501 ACTAGATGAT ATTACGGCCA TGGC 3'
```

FIG. 11

```
  1 MARRRQTGEPPLENGLIPYLGCALQFGANP
 31 LEFLRANQRKHGHVFTCKLMGKYVHPITNP
 61 LSYHKVLCHGKYFDWKKFHFATSAKAFGHR
 91 SIDPMDGNTTENINDTFIKTLQGHALNSLT
121 ESMMENLQRIMRPPVSSNKTAAWVTEGMY
151 SFCYRVMPEAGYLTIFGRDLTRRDTQKAHI
181 LNNLDNFKQFDKVFPALVAGLPIHMFRTAH
211 NAREKLAESLRHENLQKRESISELISLRMP
241 LNDTLSTFDDLEKAKTHLVVLWASQANTIP
271 ATFWSLFQMIRNPEAMKAATEEVKRTLENA
301 GQKVSLEGNPICLSQAELNDLPVLDSIKE
331 SLRLSSASLNIRTAKEDFTLHLEDGSYNIR
361 KDDIHALYPQLMHLDPEIYPDPLTFKYDRY
391 LDENGKTKTFYCNGLKLKYYYMPFGSGAT
421 ICPGRLFAIHEIKQFLILMLSYFELELIEG
451 QAKCPPLDQSRAGLGILPPLNDIEFKYKFK
481 HL *
```

GENOMIC DNA OF HUMAN CHOLESTEROL 7α-HYDROXYLASE AND METHODS FOR USING IT

CROSS REFERENCE TO RELATED APPLICATIONS

This application is a continuation of application Ser. No. 08/361,458, filed Dec. 21, 1994, which is a continuation of 08/135,488, filed Oct. 13, 1993 now abandoned. U.S. Ser. No. 135,510 "TRUNCATED HUMAN CHOLESTEROL 7α-HYDROXYLASE, METHOD OF PRODUCTION AND USE THEREOF" to Chiang, J.; and U.S. Ser. No. 135,511 "CHOLESTEROL 7α-HYDROXYLASE GENE REGULATORY ELEMENTS AND METHODS FOR USING THEM" to Chiang, J. are both filed concurrently herewith and incorporated by reference in their entirety. Additionally, the present application is related to U.S. Ser. No. 08/361,458, filed Dec. 21, 1994, which is a continuation of U.S. Ser. No. 08/135,488, filed Oct. 13, 1993, and U.S. Ser. No. 08/187,453, filed Jan. 28, 1994.

Work related to subject matter described in this application was provided by research supported in part by NIH Grant GM 31584.

BACKGROUND OF THE INVENTION

High serum cholesterol is commonly associated with an increased risk of heart attack, atherosclerosis and circulatory disorders. In addition, a variety of diseases are caused by disorders of cholesterol catabolism, such as gallstone disease, atherosclerosis, hyperlipidemia and some lipid storage diseases.

The major pathway for disposal of cholesterol in the body is by secretion of cholesterol and bile acids into the gut. Bile contains free cholesterol and bile acids. The enzyme, cholesterol 7α-hydroxylase (CYP7), commits cholesterol to bile acid synthesis and catalyzes the first and rate-limiting step of bile acid synthesis in the liver. Specifically, CYP7 catalyzes, in the presence of reductase and a reducing agent such as NADPH, the initial hydroxylation of cholesterol at the 7α-position, thereby forming 7α-hydroxycholesterol. Thus, by increasing synthesis of bile acids, this enzyme plays a key role in the liver by depleting hepatic cholesterol pools, resulting in increased LDL uptake and a lowering of serum cholesterol levels.

Bile acids are physiological agents which are important in the solubilization of lipid-soluble vitamins, sterol and xenobiotics. Bile acids are synthesized exclusively in the liver and are secreted to the intestines where they are modified to secondary bile acids. Most bile acids are reabsorbed in the ileum and recirculated to the hepatocytes via the portal vein.

The feedback of bile into the liver is known to inhibit cholesterol 7α-hydroxylase and thus inhibit the overall rate of bile acid synthesis. Cholesterol 7α-hydroxylase therefore has been a subject of intense investigations to elucidate the regulatory mechanisms of bile acid synthesis in the liver.

It is known that an interruption of bile acid reabsorption, such as that caused by the bile sequestrant, cholestyramine, or by a bile fistula, stimulates the rate of bile acid synthesis and cholesterol 7α-hydroxylase activity in the liver. It is believed that cholesterol 7α-hydroxylase activity in the liver is regulated primarily at the gene transcriptional level by bile acids, cholesterol, hormones, diurnal rhythm and other factors.

Generally, the regulation of eukaryotic genes is thought to occur at several locations, including the promoter sequences, which are located upstream of the transcription start site; enhancer or repressor sequences, which are located upstream of the promoter; within intron sequences, which are non-coding sequences located between exons or coding sequence; and in 3' sequences, which are located downstream from the coding region. The promoter sequence is unique to each gene and is required for the accurate and efficient initiation of gene transcription. Enhancers and/or repressors regulate promoter activity and determine the level of gene transcription during the development and differentiation of a particular tissue.

The promoter of most eukaryotic genes contains a canonical TATA box that binds a TFIID TATA box binding protein. TFIID complex and associated transcription activators (TAFs) interact with the basal initiation factors and RNA polymerase II to activate the promoter. The transcription complex assembly and initiation are regulated by transcription factors bound to enhancer elements located in the promoter and other regions of the gene (Pugh and Tjian, J. Biol. Chem. 267, 679–682, 1992). Tissue-specific transcription factors and nuclear steroid hormone receptors are known to play an important role in the regulation of gene expression in different tissues during development and differentiation.

However, the mechanisms underlying the regulation of cholesterol 7α-hydroxylase gene expression at the molecular level are not understood. An understanding of the regulation of CYP7 gene expression would permit development of therapeutics for treating patients with defects in bile acid synthesis and cholesterol metabolism due to altered (deficient or excessive) gene expression.

In order to study the mechanism of regulation of human cholesterol 7α-hydroxylase at the molecular level, it is therefore important to determine the correct coding, non-coding and promoter region gene sequences. An elucidation of the enzyme's gene structure, a method for analyzing promoter and enhancer/repressor activity, as well as transgenic animal models with which to study human cholesterol 7α-hydroxylase, are desired. Attempts to provide a transgenic animal expressing recombinant CYP7 have not been successful using the cDNA of CYP7. Thus, important discoveries concerning the CYP7 gene and systems for studying the CYP7 enzyme's physiology, each of which aims towards the design of therapeutic drugs and the treatment of patients with defects in bile acid synthesis and cholesterol metabolism, are highly desired.

To understand the structure and function of human CYP7 and its regulation by factors, such as bile acids, cholesterol and hormones, it is essential to purify the human CYP7 enzyme. However, the CYP7 enzyme is present in an extremely low levels in human liver; therefore, it has not been possible to isolate sufficient quantities of purified, functional enzyme from human livers.

Although a cDNA molecule encoding human CYP7 enzyme has been determined, recombinant expression of human CYP7 has not heretofore been achieved. Karam and Chiang, Biochem. Biophys. Res. Commun. 185: 588 (1992). Recently, a strategy to express a catalytically active, truncated rat cholesterol 7α-hydroxylase in E. coli was disclosed. Li and Chiang, J. Biol. Chem. 266 (29): 19186 (1991). The disclosures of both of those publications are expressly incorporated herein by reference. In the latter publication, it was disclosed that the expression of a membrane-bound hydrophobic protein in E. coli is difficult because the bacteria lacks internal membranes. Via PCR, a modified cDNA was generated that encoded a truncated enzyme lacking the N-terminal 23 amino acid residues of the rat cholesterol 7α-hydroxylase enzyme. The resulting protein was expressed, predominantly in the cytosol of the bacteria. The purified recombinant enzyme was active, as determined by its ability to hydroxylate cholesterol in a reconstituted system, and has a $K_m$ for cholesterol and $V_{max}$ similar to those of the rat microsomal (non-truncated) enzyme.

Despite the high sequence identity between the rat and human cholesterol 7α-hydroxylase, however, it previously has not been possible to express the human cholesterol 7α-hydroxylase in *E. coli* following the same strategy and using the same expression vector (pKK233-2) as that previously used for the expression of rat cholesterol 7α-hydroxylase. Thus, a catalytically active, recombinant human CYP7 enzyme is desirable. Recombinantly-expressed, truncated human CYP7 could be used to detect agents that stimulate or inhibit human CYP7's catalytic activity. Further, such recombinant protein can be used to produce anti-CYP7 antibodies which would be useful for screening assays, for example, to detect stimulated or inhibited production of human CYP7 in response to exposure of a compound to a human CYP7-producing culture.

SUMMARY OF THE INVENTION

An embodiment of the invention provides genomic DNA of cholesterol 7α-hydroxylase, in particular, DNA sequences of FIGS. 4, 5, and 6, clones λHG7α26 (ATCC 75534) and λHG7α5 (ATCC 75535), and fragments thereof.

Another embodiment provides an expression vector comprising genomic DNA of cholesterol 7α-hydroxylase and a host cell comprising the vector. Further, an expression vector can comprise a construct of a cholesterol 7α-hydroxylase promoter region operably linked to a reporter gene. Such a construct can be introduced into a mammal at an embryonic stage to provide a transgenic nonhuman mammal. Thereby, advantageously, germ cells and somatic cells of the mammal contain a promoter region from the human genomic CYP7 5' flanking sequence of the human cholesterol 7α-hydroxylase gene, wherein the promoter region is operably linked to a reporter gene.

The transgenic mammal described above containing the reporter construct can be used to screen or determine an agent's capacity to up- or down- regulate the promoter region of human cholesterol 7α-hydroxylase. This is achieved by exposing the mammal to a test agent and detecting an effect the expression of reporter gene in the mammal relative to that of a control, where no agent is applied. For example, when the mammal is exposed to agents that upregulate the promoter region of human cholesterol 7α-hydroxylase, expression of reporter gene is increased, and the agent is identified as potentially capable of decreasing serum cholesterol in humans.

Another embodiment of the invention provides a transformed cell comprising a recombinant human cholesterol 7α-hydroxylase gene which is operably linked to a cis-acting regulatory element that controls expression of said gene and wherein the recombinant human cholesterol 7α-hydroxylase gene sequence is substantially the same as the coding sequence of human cholesterol 7α-hydroxylase gene.

Another embodiment provides a cell, wherein transcription of recombinant human cholesterol 7α-hydroxylase gene is under the control of cis-acting regulatory elements/ promoter that are the same as the sequences controlling the transcription of the endogenous human cholesterol 7α-hydroxylase gene, and wherein a cis-acting regulatory element controlling transcription of said gene is inducible.

Another object of the invention is to provide a cholesterol 7α-hydroxylase minigene for transforming an animal to produce functionally active cholesterol 7α-hydroxylase. A minigene of CYP7 in this context can comprise exons I through VI inclusive and at least two introns selected from the group consisting of I and II; and I, II and III. Optionally, the minigene can further comprise a CYP7 promoter region.

Another transgenic nonhuman mammal is provided according to the invention, the mammal having germ cells and somatic cells that comprise a recombinant human cholesterol 7α-hydroxylase gene that is operably linked to a cis-acting regulatory element that controls the expression of the gene in said mammal such that peripheral blood cholesterol levels and the production of bile acids in said mammal are affected. The gene is introduced into said the non-human mammal or an ancestor of the non-human mammal at an embryonic stage, and a chromosome of said mammal includes an endogenous coding sequence substantially the same as the coding sequence of the human cholesterol 7α-hydroxylase gene. Such a transgenic mammal is provided, wherein transcription of recombinant human cholesterol 7α-hydroxylase gene is under the control of those cis-acting regulatory elements/promoter sequences that control transcription of the endogenous human cholesterol 7α-hydroxylase gene, and wherein the cis-acting regulatory element controlling transcription of said gene is inducible.

Another embodiment of the invention provides catalytically active, truncated human cholesterol 7α-hydroxylase (CYP7). Advantageously, the truncated human CYP7, which can be produced recombinantly and in relatively large recoverable amounts, has a specific activity that is at least a substantial fraction of the specific activity of truncated rat enzyme produced in accordance with Li and Chiang, *J. Biol. Chem.* 266 (29): 19186 (1991).

Another embodiment of this invention provides a catalytically active, truncated human CYP7, which lacks a membrane anchor region that is present in human CYP7. Advantageously, amino acids 1 to 24 of the membrane anchor region are deleted.

Other embodiments provide analogs of the catalytically active, truncated human CYP7 proteins of this invention.

Another embodiment comprises a fusion protein comprising catalytically active, truncated human CYP7, or a portion thereof, and a structural protein in addition to the truncated human CYP7. Advantageously, the structural protein is capable of ready expression in a particular host system such that production of truncated human CYP7 can be increased by virtue of the increased production of the structural protein.

Other embodiments provide DNA encoding the foregoing catalytically active, truncated human CYP7 proteins.

Other embodiments of the invention provide an expression vector and a host cell useful for recombinant expression of catalytically active, truncated human CYP7.

Yet other embodiments provide a method for producing catalytically active, truncated human CYP7, comprising the step of culturing a host cell according to this invention under conditions which permit production of catalytically active truncated human CYP7.

Another embodiment provides an antibody which specifically recognizes an epitope of catalytically active, truncated human CYP7.

Another embodiment provides a method for screening a compound for its effect on expression of non-truncated human CYP7. The method comprises the steps of (a) providing a host cell according to the invention under conditions which permit production of catalytically active truncated human CYP7, (b) contacting the host cell with a compound and (c) detecting the amount of catalytically active, truncated human CYP7 expressed by the host cell.

Another embodiment provides a method for screening a compound for its effect on non-truncated human CYP7 enzyme activity. The method comprises the steps of (a)contacting catalytically active, truncated human CYP7 with a compound and (b) measuring the catalytic activity of the catalytically active, truncated human CYP7.

BRIEF DESCRIPTION OF THE DRAWINGS

FIG. 1A shows a gene map of the human CYP7 gene, while FIG. 1B and FIG. 1C show the gene map of clones λHG7α26 and λHG7α5, respectively. Exons I, II and III are represented by shaded boxes. Arrows indicate regions where sequences have been determined (shown in FIGS. 4, 5 and 6).

FIG. 3 (SEQ ID NO:8) shows a human CYP7 amino acid sequence that is expressed in a transgenic animal carrying a minigene.

FIGS. 4A–4F (SEQ ID NO:9) show a nucleotide sequence, including exon I, intron I, exon II, intron II and exon III, of human CYP7.

FIGS. 5A–5B (SEQ ID NO:10) a nucleotide sequence, including 5' upstream Eco RI fragment.

FIGS. 6A–6B (SEQ ID NO:11) show a nucleotide sequence, including intron IV exon V, intron V, and exon VI, of human CYP7.

FIG. 8 (SEQ ID NO:4) provides the cDNA sequence of human CYP7. The ATG start codon is located at positions 29–31 and the TGA stop codon at positions 1475–1477.

FIG. 11 (SEQ ID NO:5) provides the truncated human CYP7 amino acid sequence.

DETAILED DESCRIPTION OF PREFERRED EMBODIMENTS

Figure 1:
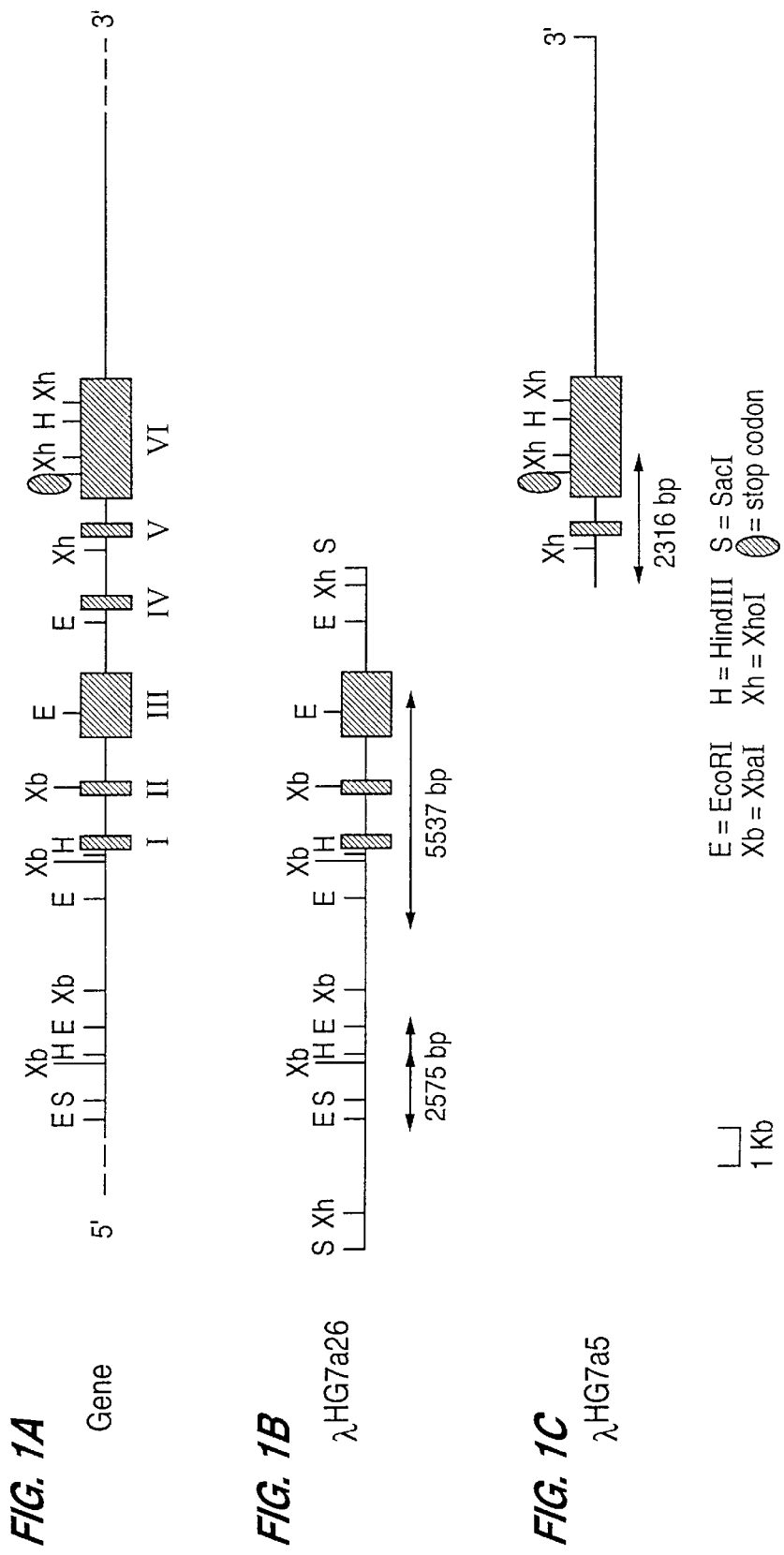

The present invention relates to the isolation and sequencing of the human genomic CYP7 gene, including intron and exon sequences and 5' upstream sequences. Two clones containing genomic CYP7 DNA are sequenced, as shown schematically in FIGS. 1B and 1C. The invention also includes a recombinant vector containing at least a fragment of the genomic CYP7 gene and a host cell, such as E. Coli, containing the vector.

The invention further includes "fragments" of the CYP7 genomic DNA, exemplified by a DNA fragment that is an exon or intron of the CYP7 gene. In FIGS. 4A–4F, exon I is nucleotides 2236 to 2319, intron I is 2320 to 3928, exon II is 3929 to 4169, intron II is 4170 to 5210, and exon III is 5211 to 5537. In FIGS. 6A–6B, partial exon IV is 1 to 456, exon V is 457 to 632, intron V is 633 to 1220, and exon VI begins at 1221 of FIGS. 6A–6B. The category of "fragment" within the present invention also encompasses any fragment obtained by digesting the disclosed DNA of the invention with any restriction endonucleases, preferably, at the restriction sites shown in FIG. 1. Other restriction fragments can be obtained as well, by using conventional skills in the art.

Also encompassed by the present invention are DNA sequences that hybridize under stringent conditions, preferably high stringent conditions, with any of the DNA sequences or fragments mentioned above. According to the present invention the term "stringent conditions" means conditions with a salt concentration of 4 × SSC (NaCl-citrate buffer) at 62°–66° C., and "high stringent conditions" means conditions with a salt concentration of 0.1 × SSC at 68° C.

From the determined gene sequence of human CYP7, a promoter region of the gene is further identified. Clone λHG7α26 contains an insert that spans about 8.0 kb of the 5'-upstream flanking sequence. According to the invention, this sequence information permits construction of a human CYP7 promoter operably linked to a reporter gene. This "promoter/reporter" gene construct is used to transform host cells and animals. For example, the promoter/reporter gene is used to transform E. coli strain JM101 or mammalian hepatocytes, or to transform a transgenic mouse or hamster.

In another embodiment of the invention, a transformed cell line or transgenic animal containing a promoter/reporter gene according to the invention is provided. Such a transformant readily detects an agent that increases or decreases expression of CYP7 gene. This is so because the agent's interaction with the CYP7 promoter region produces a corresponding reporter protein expression pattern that is easily detectable. For example, where the firefly-derived protein luciferase is used as a reporter gene, luciferase expression is measured quantitatively by its bioluminescence.

The CYP7 promoter region or certain regulatory elements excised therefrom can be used for the controlled expression of either the CYP7 gene or various reporter or indicator genes which allow quantitative determination of gene expression in the presence of inhibitory or stimulatory drugs. Reporter genes include, but are not limited to, *E. coli* β-galactosidase, galactokinase, interleukin 2, thymidine kinase, alkaline phosphatase, luciferase and chloramphenicol acetyltransferase (CAT). Such an expression system can, therefore, also be used for screening compounds for their ability to inhibit or stimulate expression of a structural gene.

In another embodiment, a minigene construct is provided by ligating a fragment of newly discovered genetic information, in particular a gene sequence excised from clone λHG7α26, together with a cDNA spanning exons 3–6. According to the present invention, a minigene is provided and used to transform an animal for in vivo production of human CYP7.

Figure 2:
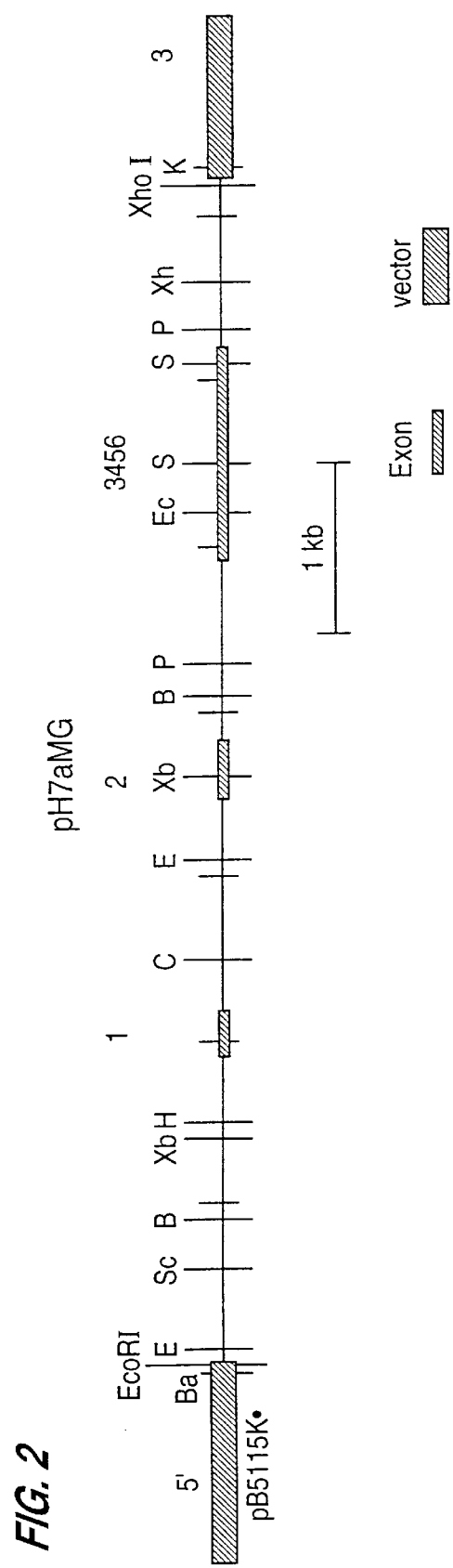
FIG. 2 is a diagrammatic representation of the construction of the human cholesterol 7α-hydroxylase containing plasmid, pH7aMG. Shaded thin boxes represent amino acid coding exons, while vector is represented by shaded thick boxes. A 5.5 kilobase EcoRI fragment (FIG. 4) which contains promoter region, exons I, II and partial exon III and introns I and II, was fused to a EcoRI-XhoI fragment of cDNA which contains partial exon III, exons IV, V and partial exon VI. An internal EcoRI site in exon III provided the linkage of the gene fragment to the cDNA to construct a minigene, as discussed in Example III. Restriction enzyme cleavage sites are as follows: Ba=BamH1, Ec=EcoR1, E=EcoR V, Sc=Sca 1, B=Bgl 11, Xb=Xba1, H=HinD111, C=Cla 1, P=Pst 1, Xh=Xho 1, S=Sma 1, K=Kpn 1.

In making a the minigene in accordance with the invention, a promoter region and exons I–VI are employed, as well as introns I and II, or introns I, II and III of the genomic CYP7 DNA. However, any of introns III, IV or V may be omitted. For example, introns III, IV and V or introns IV and V of the CYP7 gene can be omitted. Thus a preferred minigene according to the invention contains all of the CYP7 exons as well as introns I and II. Another minigene according to the invention contains all exons and introns I, II and III. Therefore, a method is provided for expressing a CYP7 gene in transgenic animals that have been transformed with a minigene, such as the minigene shown in FIG. 2.

Optionally the minigene can contain the promoter region of CYP7. Alternatively, another known promoter region is substituted for the promoter region of CYP7 to permit experimentally regulated promoter-driven expression in an animal. For example, a transgenic mouse can be made wherein the CYP7 minigene is driven by the metallothionein promoter. Use of this promoter in a transgenic mouse provides a model of CYP7 overexpression in the transgenic animal.

In another embodiment of the invention, a human CYP7 minigene permits production of a transgenic animal, preferably an animal that carries new genetic information in every tissue, including the germ cells. A minigene, when introduced into a transgenic animal, will express a CYP7 protein having an amino acid sequence shown in FIG. 3. This animal is a useful disease model for screening an agent in vivo effect on the regulation of CYP7 expression, as described further in Example 3.

Various methods are employed to introduce foreign genes into animals. These methods include: microinjection of DNA into single cell embryos, retroviral infection of embryos and calcium phosphate-mediated DNA uptake by embryonic stem cells. Hogan et al., MANIPULATING THE MOUSE EMBRYO; A LABORATORY MANUAL (Cold Spring Harbor Laboratory, 1986); Leder et al., U.S. Pat. No. 4,736,866; Leder et al., U.S. Pat. No. 5,175,383; Krimpenfort et al., U.S. Pat. No. 5,175,384, the contents of each of which are hereby incorporated by reference.

The most successful and most preferred technique is microinjection of DNA. Hammer et al., *J. Anim. Sci.* 63: 269 (1986); Gordon et al., *Science* 214: 1244 (1981); Brinster et al., *Proc. Natl. Acad. Sci. USA* 82: 4438 (1985). Microinjection involves the isolation of embryos at the single cell stage. The DNA encoding the gene of interest is microinjected in vitro into the isolated embryos and the manipulated embryos are implanted into pseudo-pregnant females. Transgenic animals can be identified shortly after birth by analyzing the DNA obtained from a tissue fragment, such as the tail, using probes specific for the inserted gene. Integration has been generally found to occur in a head-to-tail concatameric fashion at a single genomic site. Incorporation of the foreign gene at the one-celled stage results in a transgenic animal; if integration occurs at a multicellular stage, a mosaic results. Integration of two different embryonic stem cells may lead to the creation of a chimeric animal. Only microinjection results in the production of animals that can transmit the genetic information to their progeny in a Mendelian fashion. Germline integration is essential in order to utilize these transgenic animals as perpetual animal models.

Introduction of the recombinant human cholesterol 7α-hydroxylase gene at the fertilized oocyte stage ensures that the gene sequence will be present in all of the germ cells and somatic cells of the transgenic "founder" animal. The presence of the recombinant gene sequence in the germ cells of the transgenic founder animal means that approximately half of the founder animal's descendants will carry the activated recombinant gene sequence in all of their germ cells and somatic cells.

Several factors determine the level at which the new protein will be expressed, as well as its temporal and tissue-specific manner of expression. Perhaps the most important factors are the promoter and enhancer employed in controlling the expression of the protein encoded by the inserted DNA. Regulatory elements which are tissue-specific direct significant expression to a specific tissue; whereas ubiquitous promoters permit expression in different tissues within the animal.

Important cis-acting regulatory elements, other than the 5' upstream region, are required for expression of a human gene at levels equivalent to or higher than that in the unmodified organ. It is known that the first intron and second intron and possibly third intron of a human gene are important in the regulation of protein expression.

Furthermore, the presence of intronic sequences within the transgene have been shown to eliminate or at least dampen inhibitory effects of the site of DNA integration into the genome. Behringer et al., *Science* 245: 971 (1989); Lang et al., *EMBO J.* 7: 1675 (1988). For example, in order to overcome the positional effects of integration upon expression levels, the prior art has positioned enhancer regions 10–50 kb upstream, introns, or parts of introns close to splice junctions in the DNA constructs for transgenic animal production. Brinster et al., *Proc. Natl. Acad. Sci. USA* 85: 836 (1988); Buchman et al., *Mol. Cell Biol.* 8: 4395 (1988). Therefore, one of ordinary skill in this art, given the DNA sequence of the present invention, would be able to construct various combinations of cis-acting regulatory elements of the human cholesterol 7α-hydroxylase gene to test which regions are required for expression of the human gene at levels equivalent to or higher than that in the unmodified organ. The cis-acting regulatory elements of the human cholesterol 7α-hydroxylase gene to be used in such constructs are selected from: the 5' upstream region, the first intron, second intron and third intron of the human gene.

In general, the invention features a transgenic non-human vertebrate animal, preferably a mammal such as a rodent, eg., a mouse or hamster, containing germ cells and somatic cells that contain a recombinant gene which is substantially homologous with a vertebrate gene in the cholesterol 7α-hydroxylase family which is capable of expressing cholesterol 7α-hydroxylase. The recombinant gene is introduced into the animal, or an ancestor of the animal, at an embryonic stage, preferably the one-cell, or fertilized oocyte stage, and generally not later than about the 8-cell stage. The recombinant gene preferably is substantially homologous with (i.e., greater than 50% homologous, and preferably greater than 80% in terms of encoded amino acid sequence) human cholesterol 7α-hydroxylase.

Preferably, transcription of the human cholesterol 7α-hydroxylase encoding DNA is under the control of the promoter sequence that is the same as the promoter sequence controlling transcription of the endogenous coding sequence, so that the expressed protein is regulated similarly to its expression in humans. The term endogenous cis-acting regulatory elements refers to the nucleic acid sequence that controls the expression of a human cholesterol 7α-hydroxylase gene in vivo.

The animals of the invention can be used as models to test for agents that potentially effect the expression of human cholesterol 7α-hydroxylase. The use of transgenic animals to test for agents that effect: (1) the expression of various enzymes involved in cholesterol metabolism and (2) atherosclerosis is well known to those of skill in the art, as described by Breslow, *Proc. Natl. Acad. Sci. USA* 90: 8314 (1993), the entire contents of which are hereby incorporated by reference. Since human cholesterol 7α-hydroxylase is the rate limiting enzyme controlling peripheral blood cholesterol levels, the consequent occurrence of hypercholesterolemia in humans is dependent upon the levels at which this enzyme is expressed. Hypercholesterolemia (or hypercholesteremia or hypercholesterinemia) is a clinical condition in which there is an abnormally large amount of cholesterol present in the cells and plasma of the circulating blood. Hypercholesterolemia is a serious medical condition that leads to atherosclerosis, atheromatous plaques, arteriole sclerotic plaque formation, hypertension and heart disease. The transgenic animals of the invention can be used for testing agents that may cure hypercholesterolemia, or relieve its symptoms, or for testing agents that may promote hypercholesterolemia.

The agents to be tested can be administered to an animal of the invention and the animal's peripheral cholesterol and bile acids are monitored. Peripheral cholesterol is measured by routine tests available in most clinical laboratories. Bile acid production is monitored using reverse phase high pressure liquid chromatography (HPLC).

Transgenic animals of the invention are most useful as animal models for testing agents and procedures that promote or inhibit overexpression or under expression of CYP7. Overexpression would result in increased bile acid synthesis from cholesterol whereas underexpression would result in decreased bile acid synthesis from cholesterol and hypercholesterolemia. Therefore, transgenic animals of the invention may be used to study the regulation of bile acid synthesis and hypercholesterolemia. In particular, a transgenic mouse or hamster on a high cholesterol diet is used to determine whether overexpression of CYP7 in the mice could prevent hypercholesterolemia. Transgenic mice fed a diet containing high levels of both bile acids and cholesterol are used to determine whether a high bile acid diet suppresses 7α-hydroxylase expression and thus induces hypercholesterolemia.

The constructs of the present invention may be used to assess gene expression in vitro as well as gene regulation in vivo. For example, the construct of FIG. 2 may be used to transfect hepatocytes and other mammalian cells to test for tissue specific expression of the CPY7 gene. Also, the construct of FIG. 7 may be used to transfect hepatocytes and other mammalian cells to assess the regulation of the CPY7 gene.

In general, the invention features a transformed mammalian cell, preferably a hepatocyte, containing a recombinant gene which is substantially homologous with a vertebrate gene in the cholesterol 7α-hydroxylase family which is capable of expressing cholesterol 7α-hydroxylase. The recombinant gene is introduced into the cell by various transfection means well known in the art. The recombinant gene preferably is substantially homologous with (i.e., greater than 50% homologous, and preferably greater than 80% in terms of encoded amino acid sequence) human cholesterol 7α-hydroxylase.

Preferably, transcription of the human cholesterol 7α-hydroxylase encoding DNA is under the control of the promoter sequence that is the same as the promoter sequence controlling transcription of the endogenous coding sequence, so that the expressed protein is regulated similarly to its expression in humans.

The cells of the invention can be used as models to test for agents that potentially effect the expression of human cholesterol 7α-hydroxylase. The agents to be tested can be provided to the cells and the expression of human cholesterol 7α-hydroxylase assayed. Such transformed cells are useful for testing agents that promote or inhibit overexpression or under expression of CYP7.

Analysis of the CYP7 promoter may be performed in cell culture using either the downstream recombinant CYP7 minigene or a reporter construct. The CYP7 regulatory elements can be used for the controlled expression of either the CYP7 gene or various reporter or indicator genes which allow quantitative determination of gene expression in the presence of inhibitory or stimulatory drugs. Reporter genes and systems have been described herein.

In another related discovery, it has been found surprisingly, that catalytically active, truncated human CYP7 now can be expressed recombinantly. This is achieved by using a bacterial strain having the characteristics of the *E. coli* strain TOPP3, and a vector having the characteristics of the expression vector pJL. No other bacteria strains or expression vectors have been found that possess the characteristics permitting expression of the truncated human CYP7 enzyme. In particular, "*E. Coli* TOPP3-pJL/H7α1.5" contains the expression vector pJL/H7α1.5 DNA and encodes a truncated human CYP7 cDNA that is expressed in relatively large amounts in the bacterial cytosol.

Therefore, one embodiment of the present invention is a catalytically active, truncated human CYP7 protein. "Truncated" as used herein means that a portion, all or substantially all of the complete membrane anchor region of human CYP7 has been deleted. Advantageously, all or a substantial portion of amino acids 1 to 24, which comprise the membrane anchor region in human CYP7, are deleted. FIG. 11 provides the amino acid sequence of a catalytically active, truncated human CYP7 protein in accordance with this invention.

By "catalytically active" it is meant that the CYP7 protein is capable of catalyzing, in the presence of reductase and a reducing agent such as NADPH, the initial hydroxylation of cholesterol at the 7α-position, thereby forming 7α-hydroxycholesterol. Catalytic activity can be measures in known assays using several well known parameters such as $K_M$ and $V_{Max}$. Advantageously, catalytic activity can be measured as specific activity and compared with the specific activity of the catalytically active, truncated rat CYP7 discussed above. Most advantageously, specific activity of the truncated human CYP7 and the truncated rat CYP7 are measured in simultaneously run assays under identical conditions. Otherwise, assay-to-assay variations in activity may be observed by virtue of differences in the assay conditions.

Also encompassed by the invention is an analog of catalytically active, truncated human CYP7. In accordance with this invention, the term "analog" includes a protein having conservative amino acids substitutions or deletions that do not eliminate the enzymatic activity of the truncated human CYP7. Advantageously, the analog retains a specific activity that is at least about ten percent (10%) of the specific activity of truncated rat CYP7 produced in accordance with Li and Chiang, *J. Biol. Chem.* 266: 19186 (1991).

Skilled artisans will readily appreciate that an analog of catalytically active, truncated human CYP7 having the amino acid sequence in FIG. 11 readily can be constructed. The analog can be the prepared, for example, by exploiting the degeneracy in the genetic code, or by effecting a point mutation which yields an amino acid substitutions and/or additions or deletions of non-essential amino acids. Advantageously, the amino acid substitutions can be conservative in accordance with well known principles.

By way of example, an analog advantageously includes those proteins having at least about 85%, and more advantageously at least about 90% amino acid sequence homology, which proteins still possesses substantially similar enzymatic activity as that of the truncated rat CYP7. Advantageously, the catalytically active, truncated human CYP7 or analog thereof will possess at least about 10%, advantageously at least about 25%, more advantageously at least about 50%, more advantageously at least about 75%, and more advantageously at least about 90% of the specific activity of catalytically active, truncated rat CYP7 as measured in simultaneous assays run under identical conditions.

The present invention further includes a fusion protein comprising catalytically active, truncated human CYP7, or a portion thereof, and a structural protein in addition to the truncated human CYP7. Advantageously, the structural protein is capable of ready expression in a particular host system. Advantageously, the structural protein is a protein which is produced in relatively high quantity by the host. In this way, production of truncated human CYP7 can be increased by virtue of the increased production of the structural protein. Thus a vector is provided that in addition to a truncated hCYP7 gene, such as H7α1.5, further contains a gene encoding at least one additional structural protein. The additional protein is advantageously selected from among proteins that are expressed at high levels in *E. coli*, including factor IX, for example. See Nagai et al., *Meth. Enzym.* 153: 461 (1987), the contents of which are hereby expressly incorporated by reference.

Additional embodiments of this invention comprise DNAs which encode the proteins described herein. Those skilled in the art will appreciate that many different DNAs can encode a single protein, and preferred codons routinely can be employed for different expression systems. All such DNAs are contemplated within this invention. Further, within this embodiment are DNA sequences that hybridize under stringent conditions, preferably under highly stringent conditions, with the DNA sequence encoding catalytically active, truncated human CYP7. According to the present invention the term "stringent conditions" means hybridization conditions comprising a salt concentration of 4× SSC (NaCl-citrate buffer) at 62°–66° C., and "high stringent conditions" means hybridization conditions comprising a salt concentration of 0.1× SSC at 68° C.

Yet another embodiment of the invention provides a method of making catalytically active, truncated human CYP7 protein recombinantly. One method comprises culturing a host cell containing the gene encoding the protein or an analog thereof, advantageously *E. coli* TOPP3 (ATCC 69401), under conditions which permit production of the protein. Advantageously, the method further comprises the step of recovering quantities of protein. Advantageously, as discussed below, high quantities of the polypeptide are obtained. Skilled artisans will appreciate the various ways in which recombinant proteins of this invention can be prepared.

Compared to a corresponding amount of rat CYP7 produced according to Li and Chiang, *J. Biol. Chem.* 266: 19186 (1991), the level of truncated human CYP7 expressed according to the invention is increased substantially, i.e., by a four-fold increase in yield. According to the present invention, a method is provided for obtaining expression of at least 30 nmol human cholesterol 7α-hydroxylase in one liter of *E. coli* culture, but more advantageously, 50 nmol/ liter. This markedly improved yield can be achieved by subcloning the cDNA in a pJL expression vector to form pJL/R7α1.5, which can then be transformed into *E. coli* strain TOPP3. The pJL expression vector is characterized by possessing (i) a transcription enhancer sequence, located upstream from and proximal to a ribosomal binding site, and (ii) an origin of replication for pUC12.

Another embodiment of this invention is an expression vector containing the DNA encoding truncated CYP7, especially an expression vector additionally containing a transcription enhancer region (T.E.), particularly wherein said T.E. is located upstream from and proximal to a ribosomal binding region. Preferably, the vector also has an origin of replication for pUC12 as well, or some other origin known to be associated with the expression of high copy numbers of an inserted gene. Typically, the T.E. and the ribosomal binding region are operably attached to the truncated CYP7 cDNA. An advantageous embodiment of the present invention includes the expression vector pJL/H7α1.5 containing DNA encoding truncated CYP7 and the transfected *E. coli* TOPP3 (ATCC 69401) as a host cell.

Also included is a method of making a truncated CYP7 protein that employs an expression vector containing a transcription enhancer region (T.E.), particularly wherein said T.E. is located upstream from and proximal to a ribosomal binding region and which preferably has an origin of replication for pUC12. This method can be exploited to make truncated CYP7 proteins having a species origin other than human or rat. Thus, for example, hamster, murine and other species of truncated CYP7 made by using an expression vector (without the human gene insert) and an *E. coli* TOPP3 host cell are encompassed by the invention. In particular, according to the present invention, *E. coli* TOPP3 transfected with a pJL expression vector containing a CYP7 genomic insert of the desired species of CYP7 is used to produce another species of truncated CYP7.

*E. coli* TOPP3-pJL/H7α1.5 was deposited on Aug. 25, 1993, at the American Type Culture Collection, ATCC, 12301 Parklawn Drive, Rockville, Md. 20852, U.S.A. under the accession number ATCC 69401.

Also included in the present invention are monoclonal and polyclonal antibodies, or binding fragments thereof, specific for truncated human CYP7, i.e., which specifically recognize an epitope of catalytically active, truncated human CYP7. Methods for the preparation of such antibodies are also contemplated (see Example 11 below). Further, an anti-truncated CYP7 antibody can be used in a method to screen compounds for their ability to inhibit or stimulate CYP7 enzyme expression (see Example 11). For example, either an antibody according to the invention or an antibody against non-truncated human CYP7 is used to detect the expression of truncated human CYP7 in an assay. Thus, to screen for an agent that enhances CYP7, an agent can be added to a culture of TOPP3-pJL/Hα1.5 for a period of time sufficient for the agent to modulate expression, after which expressed truncated human CYP7 is detected using any of the above-described antibodies in a Western blot. An increase in protein content, relative to the level of control enzyme expression from cells not exposed to the agent, detects an agent that stimulates expression of human CYP7. Results of such as assay optionally are confirmed with an in vivo transgenic animal assay, as described herein.

Truncated CYP7 obtained according to the present invention also can be used in a screening assay as an indicator of non-truncated CYP7 activity. A compound can be screened to determine whether it increases or decreases either the level of enzyme expression or its activity. A compound can be tested either alone or in the presence of physiological agents or drugs (see Examples 10 and 11). Information obtained can be used to screen for potentially beneficial drugs, and particularly for the design of drugs capable of treating patients with defects in bile acid synthesis and cholesterol metabolism.

A compound screening method according to the present invention can be performed as follows. To assess a compound's effect on CYP7 enzyme activity in human liver, the compound, in varying dosages, is tested in the enzyme assay method. Such a method, is advantageously performed on truncated CYP7, purified from E. coli TOPP3-pJL/H7α1.5. A method for detecting the enzyme's activity is described in Example 10 herein. A compound's effect on CYP7 enzyme levels is determined, for example, using a CYP7 specific antibody in a Western blot assay, as described in Example 11.

The following examples illustrate the invention and, as such, are not to be considered as limiting the invention set forth in the claims.

EXAMPLE 1

Genomic DNA of CYP7 Human Cholesterol 7α-hydroxylase

A human genomic library constructed with Sau3A1 partially digested human placental DNA ligated into a BamHI site of EMBL-3 Sp6/T7 phage vector (Clontech, Palo Alto, Calif.) was screened using a 1.6 kb EcoRI-PstI fragment of a human cholesterol 7α-hydroxylase cDNA isolated previously (Keram and Chiang, Biochem. Biophys. Res. Comm. 185, 588–595, 1992) as a hybridization probe. Hybridizations were carried out at a high stringent condition of 68° C., 1% SDS and 0.1× SSC. 800,000 pfu of phages were screened. After four cycles of screening, seven positive clones were plaque-purified. Three clones containing the largest inserts (λHG7α26, λHG7α5 and λHG7α52) were isolated and analyzed by restriction mapping. FIG. 1B shows the gene map of clone λHG7α26, which contains a 15 kb insert that spans about 8.0 kb of the 5'-upstream flanking sequence and exons I to III (FIGS. 4A–4F and 5A–5B). Clone λHG7α5 (FIG. 1C) contains intron IV, exon V, intron V and partial exon VI (FIGS. 6A–6B). An 8.0 kb 3'-flanking sequence extends beyond the sequenced region of λHG7α5 (FIG. 6).

Bacteriophage clones λHG7α26 and λHG7α5 both were deposited Aug. 25, 1993 at the American Type Culture Collection, ATCC, 12301 Parklawn Drive, Rockville, Md. 20852, USA under the accession numbers ATCC 75534 and ATCC 75535, respectively.

Five EcoRI fragments of the clone λHG26 were excised from the phage DNA insert by restriction digestion and shotgun subcloned into phagemid vector pBluescript II KS+ (Stratagene, La Jolla, Calif.). The clones were size-selected and EcoRI fragments were isolated from CsCl purified plasmids and used for sequencing. Nested deletions were generated by ExoIII/Mung Bean nuclease digestion according to manufacturer's instruction (Stratagene, Calif.) using the conditions of 37° C. incubation for 1 min intervals. This condition resulted in an average deletion of about 200 to 250 bp/min. DNA sequencing of the nested deletions were carried out by the dideoxy chain termination method using T7 sequenase version 2.0 (USB, Cleveland, Ohio) and $^{35}$S-dATP. Sequence data were obtained from both strands and the overlapping deletion clones and analyzed using DNASIS software (Hitachi America, Calif.).

Nucleotide sequences of a 5 kb EcoRI fragment and a 2.6 kb EcoRI fragments were determined. The 5 kb fragment contains the sequence from −1886 of the 5'-upstream region to partial exon 3 (FIGS. 4A–4F). Included in FIGS. 4A–4F is a 347 bp 3'-end sequence of a 3.5 Kb EcoRI fragment located immediately upstream of this 5 Kb fragment and a 233 bp 5' end sequence of a 2.6 kb EcoRI fragment immediately downstream of a 5 kb fragment. As shown in FIG. 1B, the 2.6 kb fragment (FIGS. 5A–5B) is located further 5' of the 3.5 kb EcoRI fragment. Thus, about 4875 bp of the 5'-upstream flanking region sequence of the gene were determined.

A comparison of sequences of the present invention to those of Molowa et al. (1992) in the overlapping region (1604 bp) revealed that sequences from the transcription start site to about −460 are identical; however, further upstream sequences vary significantly. A total of 52 sequence discrepancies were found, not all of are attributed to the presence of polymorphisms in the human genes. Cohen at al. (Genomics, 14, 153–161, 1992) reported a 723 bp upstream sequence. Seven mismatches in Cohen's sequence from +1 to −723 were identified. A "T" to "C" conversion at nucleotide −469 was identified to be a Mae II polymorphism (Thompson et al., Biochem. Biophys. Acta. 1168, 239–242, 1993). The 5'-flanking sequence of the present invention was identical to that reported by Thompson et al., (1993), with the exception of a mismatch at nucleotide −1197, found in the overlapping region from +1 to nucleotide −2235. No intron sequences have been reported by other laboratories.

Clone λHG7α5 was also sequenced from the 5' end of the gene. FIGS. 6A–6B is the 2316 basepair sequence that contains partial intron IV, exon V, intron V and exon VI of the human CYP7 gene.

EXAMPLE 2

Promoter/Reporter Transgenic Animal

Figure 7:
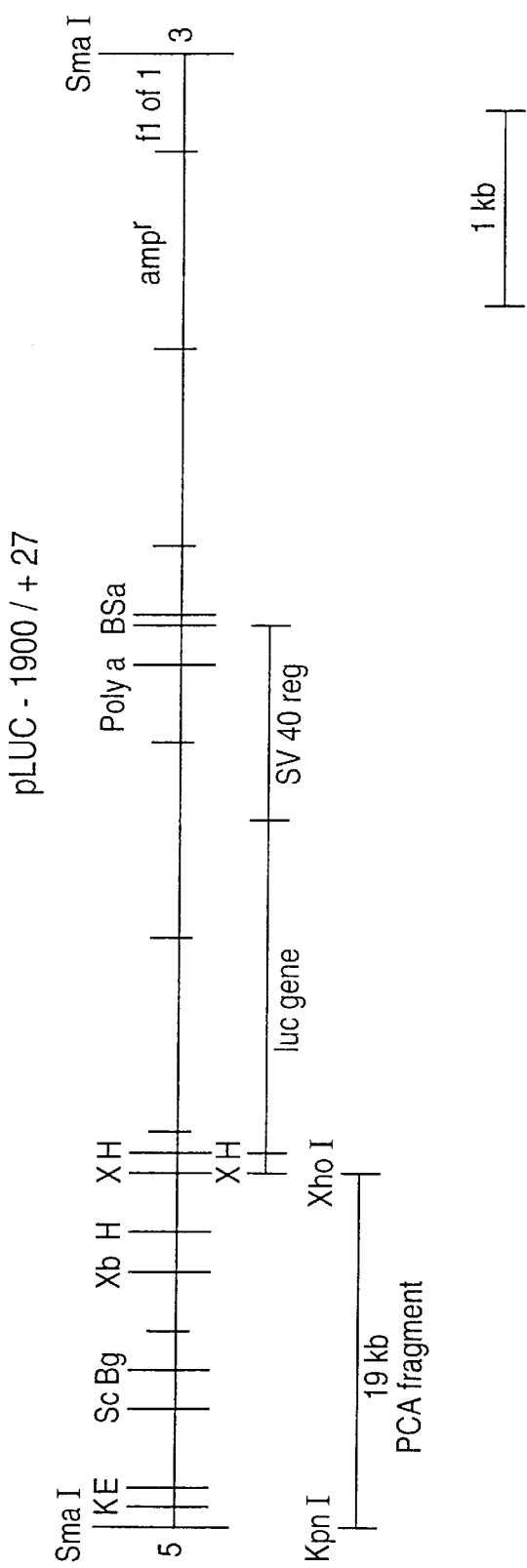
FIG. 7 is a diagramatic representation of the construction of the luciferase reporter gene vector that includes the 5' sequence from the human genomic cholesterol 7α-hydroxylase gene, and the reporter luciferase gene described in Example 2. Restriction enzyme cleavage sites are as follows: K=Kpn 1, E=EcoR1, Sc=Sca 1, Bg=Bgl 11, Xb=Xba 1, H=Hind 111, X=Xho 1, B=BamH1, Sa=Sa1 1.

Assessment of gene regulation in transgenic animals using the luciferase reporter system is well known to those of skill in the art. DiLelia et al., Nucl. Acids. Res. 16: 4159 (1988), incorporated by reference in its entirety. Vectors for producing such reporter constructs are commercially available from Promega Corporation (2800 Woods Hollow Road, Madison Wis. 53711–5399). For example, the pGL2-Basic luciferase vector (Promega) may be used to construct a cassette that will report the important cis-acting elements in the CYP7 5' sequence from the human genomic cholesterol 7α-hydroxylase gene. As shown in FIG. 7, a 1.9 kb promoter region of the human genomic clone HG7α26 from −1879 to +24, which is equivalent to nucleotides 2236 through 4139 of FIGS. 4A–4F, was obtained by PCR amplification. A Kpn 1 site was introduced at the 5' end using an HLU-1 primer (HLU-1 primer =5'TACCGCTCGAGTGATTAGAAAGGGAAGGAT 3') (SEQ ID NO:6) and an Xho 1 site was introduced at the 3' end using an HLU-2 primer (HLU-2 primer= 5'CAAGAATGATAGATAAAAT 3') (SEQ ID NO:7). This recombinant Kpn 1-Xho 1 fragment containing the human cholesterol 7α-hydroxylase promoter region was ligated into the luciferase vector pGL2-Basic (Promega), which had been cut with restriction enzymes Kpn 1 and Xho. The resulting promoter-luciferase reporter chimeric construct was purified and used to transform host cells, such as the *E. coli* strain JM101.

The entire 1.9 kb human cholesterol 7α-hydroxylase promoter region and luciferase reporter gene, including a poly(A) signal, is flanked by unique Kpn 1 and BamH 1 restriction enzymes sites. The Kpn 1 and BamH1 fragment is 4.6 kb and is used for microinjection into fertilized oocytes in the production of transgenic animals. Transgenic animals containing this construct, as assayed by Southern Blot analysis, are then tested for various agents which are capable of upregulating or downregulating the CYP7 cis acting elements. Alternatively, given the DNA sequence of the present invention, one of skill in the art is able to contruct various combinations of cis-acting regulatory elements of the human cholesterol 7α-hydroxylase gene to test the specific regions and positional affects that are required for expression of the human cholesterol 7α-hydroxylase gene at levels equivalent to or higher than that in the unmodified organ. The cis-acting regulatory elements of the human cholesterol 7α-hydroxylase gene to be used in such constructs are selected from: the 5' upstream region, the first intron, second intron and third intron of the human gene.

Tissue samples, including liver, are tested for luciferase activity by methods well known in the art. *Promega Notes* 28:1 (1990); *Promega Technical Bulletin* (Promega Corporation, September 1993); Wood, BIOILLUMINESCENCE AND CHEMILUMINESCENCE (John Wiley and Sons, 1991). Briefly, the homogenized tissue supernatants are mixed with luciferin and Coenzyme A in a buffer containing ATP. Luciferin illuminescence, as detected using a luminometer, only occurs in the presence of the recombinant luciferase expressed in the transgenic tissue.

EXAMPLE 3

Production & Analysis of Transgenic Mice Containing DNA Encoding Human Genomic Cholesterol 7A-hydroxylase The recombinant CYP7 minigene present in the pH7aMG vector is incorporated into the germ cells of mice as follows: The construction of the pH7aMG shown diagrammatically in FIG. 2. The entire 7.2 kb insert in pH7aMG can be removed by restriction enzyme cleavage with BamH 1 and Kpn 1. The CYP7 minigene DNA was prepared for injection by digestion with 4 units each of BamH1 and Kpn1 per ug of DNA per 1 hour at 37° C., electrophoresed through a 1% agarose gel, and purified as described by Sinn et al., *Cell* 49: 465 (1987). The isolated 7.2 kb DNA fragment was injected into the pronuclei of fertilized one-cell mouse or hamster eggs derived from the FVB/NHd inbred strain (Taconic laboratory, Germantown, N.J.). About 100 to 1000 copies of linearized plasmid is incorporated per pronucleus. Following microinjection, viable eggs are transferred to the oviducts of pseudopregnant Swiss Webster mice (Taconic Farms), as described by Wagner et al., *Proc. Natl. Acad. Sci. USA* 78: 5016 91981). Mice are housed in an environmentally controlled facility maintained on a 10 hour dark: 14 hour light cycle. The eggs in the foster females are allowed to develop to term.

Between two and six weeks of age, the DNA of each pup born is analyzed by Southern hybridization using DNA taken from the pup's tail. DNA is extracted from 1.5 cm tail sections. Davis et al. *Meth. Enzym.* 65: 405 (1980). The nucleic acid pellet is resuspended in 200 μl of 10 mM Tris-Cl pH 7.4, 0.1 mM EDTA, and 10 μg is digested with Kpn1 and BamH$_1$, electrophoresed through 1.0% agarose, and transferred to nitrocellulose. Southern, *J. Mol. Biol.* 98: 503 (1975). Filters are hybridized overnight to CYP7 transgene specific probe in the presence of 10% dextran sulfate and washed twice in 2× SSC, 0.1% SDS at 64° C. A CYP7 transgene specific probe is a fragment of the CYP7 minigene that will not hybridize to related sequences in the host genome. This fragment is free of repetitivesequences. The CYP7 transgene specific probe is labeled with $^{32}$P dCTP by nick translation. Rigby et al., *J. Mol. Biol.* 113: 237 (1977).

Southern hybridization indicates which founder mice retain the CYP7 minigene construct.

3.1 Transcription of the Human Cholesterol 7α-hydroxylase Minigene in Transgenic Mice Transcription of the newly acquired gene in tissues was determined by extracting RNA from the tissues and assaying the RNA by Northern Blot analysis. The excised tissue is rinsed in 5.0 ml cold Hank's buffered saline and total RNA is isolated by methods employing a CsCl gradient. Chirgwin et al. *Biochem.* 18: 5294 (1979). RNA pellets are washed twice by reprecipitation in ethanol and quantitated by absorbance at 260 nm. Single stranded, uniformly labeled RNA probe is prepared using a transgene specific probe. Such a transgene specific probe is a fragment of the CYP7 minigene that will not hybridize to related sequences in the host genome. This fragment is free of repetitive sequences. Since the human cholesterol 7α-hydroxylase mRNA is 3 kb and the endogenous mouse cholesterol 7α-hydroxylase mRNA is 4 kb, even the entire CYP7 minigene construct cut out of the pH71MG could be used to identify the presence of the transcribed exogenous human cholesterol 7α-hydroxylase gene. Melton et al., *Nucl. Acids Res.* 12:7035 (1984).

To test for transcription of the CYP7 minigene, labelled single-stranded probe fragments are isolated on 8M urea 5% acrylamide gels, electroeluted and hybridized to total RNA. Berk et al., *Cell* 12: 721 (1977). The hybridization mixture contains 50,000 CPM to 100,000 cpm of probe (Specific Activity—$10^8$ cpm/ug), 10 μg total cellular RNA, 50% formamide, 500 mM NaCl, 20 mM Tris pH 7.5, 1 mM EDTA. Melton et al. (1984) supra. Hybridization temperatures vary according to the GC content. The hybridizations are terminated by the addition of 1500 units of RNAase A and RNAase T$_1$ (Sigma, St. Louis, Mo.). RNAase digestions are carried out at 37° C. for 15 minutes. The samples are then ethanol precipitated and electrophoresed on 8M urea 5% acrylamide gels.

The tissues analyzed are liver, muscle, pancreas, stomach, brain, intestines, eye, aorta, salivary gland and kidney. 10 μg of total RNA from each of these tissues is analyzed using a transgene specific probe.

In situ hybridization, using the transgene specific probe, of the histologic sites that transcribe the CYP7 minigene confirm the presence of the exogenous cholesterol 7α-hydroxylase gene in the transcribing tissues.

3.2 Localization of Transgene Expression mRNA transcripts are evaluated in liver RNA (prepared as above) after conversion to cDNA, PCR amplification and Southern hybridization analysis. Rosenfeld et al., supra. To ensure that CYP7 transgene is specifically evaluated and that the 5' and 3' portion of mRNA transcripts are present, two separate primer pairs are used: a 5' primer pair to detect the 5' end of recombinant construct MRNA transcripts and a CYP7-specific antisense primer, and a 3' primer pair to evaluate the 3' end of the recombinant mRNA transcript. Fiers et al., *Nature* 273: 113 (1978)

PCR amplification products are evaluated by agarose gel electrophoresis followed by Southern hybridization using $^{32}$P-labeled human CYP7 probes.

Northern analysis of liver RNA from transgenic animals will exhibit CYP7 directed human mRNA transcripts of a size similar to that directed by these constructs in cultured cells. Levels of a constituitively expressed protein transcripts, such as Beta-actin or glyceraldehyde-3-phosphate dehydrogenase, serve as a positive control and are normally similar for both transgenic and nontransgenic tissue samples.

3.3 Expression of Recombinant Human Cholesterol 7α-hydroxylase in Transgenic Animal Tissues Expression of the human cholesterol 7α-hydroxylase transgene is evaluated by Western Blotting or immunohistochemistry. Alternatively, expression of a linked reporter gene, such as luciferase or LAC-Z, may be used to quantitate the tissues or cells expressing the transgene. For western blot or immunohistochemical detection of transgenically expressed protein, antibodies specific for human cholesterol 7α-hydroxylase are used to detect the presence of this enzyme in various tissue sections or protein preparations from various tissues. Antibodies specific for human cholesterol 7α-hydroxylase are described in J. Chiang (Attorney docket 18748/176, U.S. Ser. No. 08/135,510). Briefly, 1 mg purified CYP7 enzyme is mixed with an equal volume of Freund's adjuvant and 5 mg/ml of heat-killed microbacteria. The emulsified antigen mixtures were injected on the back of New Zealand white rabbits by intradermal injections on multiple sites. After six weeks, 0.5 mg of purified human enzyme was mixed with incomplete adjuvant and used for booster injections to the same rabbits. Six weeks later, blood samples were collected from ear veins and tested for the presence of antibodies by Ouchterlony double diffusion and by immunoblotting as described previously by Chiang, et al., *J. Biol. Chem.* 265, 3889–3897 (1990), incorporated by reference in its entirety. For immunoblot analysis, one µg of purified human CYP7 enzyme was loaded on a 7.5% SDS-polyacrylamide gel, separated polypeptides were electrophoretically transferred to an Immobilon P membrane by a modified procedure reported previously (Chiang et al., supra. (1990)). Diluted antisera were reacted with membrane and subsequently reacted with second antibody, anti-rabbit IgG conjugated with alkaline phosphatase, and then stained with nitroblue tetrazolium (NBT) and 5-bromo-4-chloro-3-indolylphosphate (DCIP) as described previously.

The presence of human 7 alpha-hydroxylase expression in tissues is evaluated by immunohistochemistry using a human 7 alpha-hydroxylase specific antibody. The alkaline phosphatase monoclonal anti-alkaline phosphatase method is used to detect binding of the specific antibody to various tissue sections.

EXAMPLE 4

Animal Testing

Transgenic animals of the invention are most useful as animal models for testing agents and procedures that promote or inhibit overexpression or under expression of CYP7. The CYP7 expressing animals are tested for materials that are suspected of promoting or inhibiting hypercholesterolemia. The animals are exposed to various dosages of a known agent and tested for peripheral blood cholesterol and bile acid production. Animals and their descendants that have either increased or decreased peripheral blood cholesterol levels are then tested for the effect of an agent on the expression of CYP7.

Transgenic animals treated with agents that cause overexpression of CYP7 are used to study whether such overexpression prevents hypercholesterolemia when such treated animals are on a high cholesterol diet. Also, transgenic mice fed a diet containing high levels of both bile acids and cholesterol are used to determine whether a high bile acid diet suppresses 7α-hydroxylase and thus induces hypercholesterolemia.

EXAMPLE 5

Tissue Culture of Transgenic Cell Lines

The transgenic animals of the invention can be used as a source of cells for cell culture. Cells of the tissues of the transgenic animal that contain the activated recombinant gene can be cultures, using standard tissue culture techniques and used, for example to study the causes of hypercholesterolemia at the cellular and tissue level.

EXAMPLE 6

Production of Transformed Cells: Promoter/Reporter Gene Constructs

Assessment of gene regulation in transformed mammalian cells using the luciferase reporter system is well known to those of skill in the art. deWet et al., *Mol. Cell. Biol.* 7: 725 (1987). The same pGL2-Basic luciferase vector (Promega) constructs described for the transgenic animals may be used in vitro. Also, luciferase activity in cell culture is performed by methods well known in the art. *Promega Notes* 28:1 (1990); *Promega Technical Bulletin* (Promega Corporation, September 1993). Briefly, the supernatants of lysed cells are mixed with luciferin and Coenzyme A in a buffer containing ATP. Luciferin illuminescence, as detected using a luminometer, only occurs in the presence of the recombinant luciferase expressed in the transformed cells.

The transformed promoter-reporter cells of the invention can be used as models to test for agents that potentially effect the expression of human cholesterol 7α-hydroxylase.

To determine the promoter sequences responsible for regulation of cholesterol 7α-hydroxylase, deletions of the human CYP7 cis-acting elements are ligated upstream of the luciferase reporter gene (Luc). The promoter fragments were generated by the polymerase chain reaction using the primers and a human CYP7 genomic clone as the template. The fragments were blunted by filling in with the Klenow fragment of DNA polymerase and then digested with Xho I. The fragments were then ligated into pGL2-basic vector (Promega) which had been digested with SmaI and Xho I, and transformed into *E. coli* HB101 cells. The resulting plasmids could be used to transfect primary hepatocytes or hepatoma cells for the study of human luciferase gene expression under the control of the human CYP7 promoter.

Chloramphenicol acetyltransferase (CAT) reporter gene constructs were made by using the polymerase chain reaction and primers to amplify the 5' flanking regions and introns 1, 2 and 3 of the human CYP7 gene. Fragments are ligated into a promoterless pCAT basic vector (Promega). This plasmid is then used to generate nested deletions containing various pieces of 5' flanking DNA, intron 1, intron 2 and/or intron 3.

EXAMPLE 7

Production of Transformed Cells: Minigene Contructs

The DNA of each transformed cell line from each construct is analyzed by Southern hybridization. DNA is extracted from the cells culture and the nucleic acid pellet is resuspended in 200 ul of 10 mM Tris-Cl pH 7.4, 0.1 mM EDTA, and 10 ug is digested with Kpn1 and BamH1, electrophoresed through 1.0% agarose, and transferred to nitrocellulose. Southern, J. Mol. Biol. 98: 503 91975). Filters are hybridized overnight to CYP7 transgene specific probe in the presence of 10% dextran sulfate and washed twice in 2× SSC, 0.1% SDS at 64° C. A CYP7 transgene specific probe is a fragment of the CYP7 minigene that will not hybridize to related sequences in the host genome. This fragment is free of repetitive sequences. The CYP7 transgene specific probe is labeled with $^{32}$P dCTP by nick translation. Rigby et al., *J. Mol. Biol.* 113: 237 (1977). Southern hybridization indicates cell lines contain the CYP7 minigene construct.

Transcription of the newly acquired gene in cultured cells is determined by extracting RNA from the cells and assaying the RNA by Northern Blot analysis, as described above.

Expression of recombinant human cholesterol 7α-hydroxylase in cell culture is evaluated by Western Blotting or immunocytochemistry. Alternatively, expression of a linked reporter gene, such as luciferase or LAC-Z, may be used to quantitate the tissues or cells expressing the transgene. For western blot or immunocytochemical detection of the recombinant protein, antibodies specific for human cholesterol 7α-hydroxylase are used to detect the presence of this enzyme in the various transformed cells.

In Vitro Agent Testing

Transformed cell lines of the invention are most useful as in vitro models for testing agents and procedures that promote or inhibit overexpression or under expression of CYP7. The CYP7 expressing cell lines are tested for materials that are suspected of promoting or inhibiting hypercholesterolemia. The cells are exposed to various dosages of a known agent and tested for the presence of human cholesterol 7α-hydroxylase.

EXAMPLE 8

Production and Expression of Truncated Human Cholesterol 7α- hydroxylase in *E. Coli*

Figure 9:
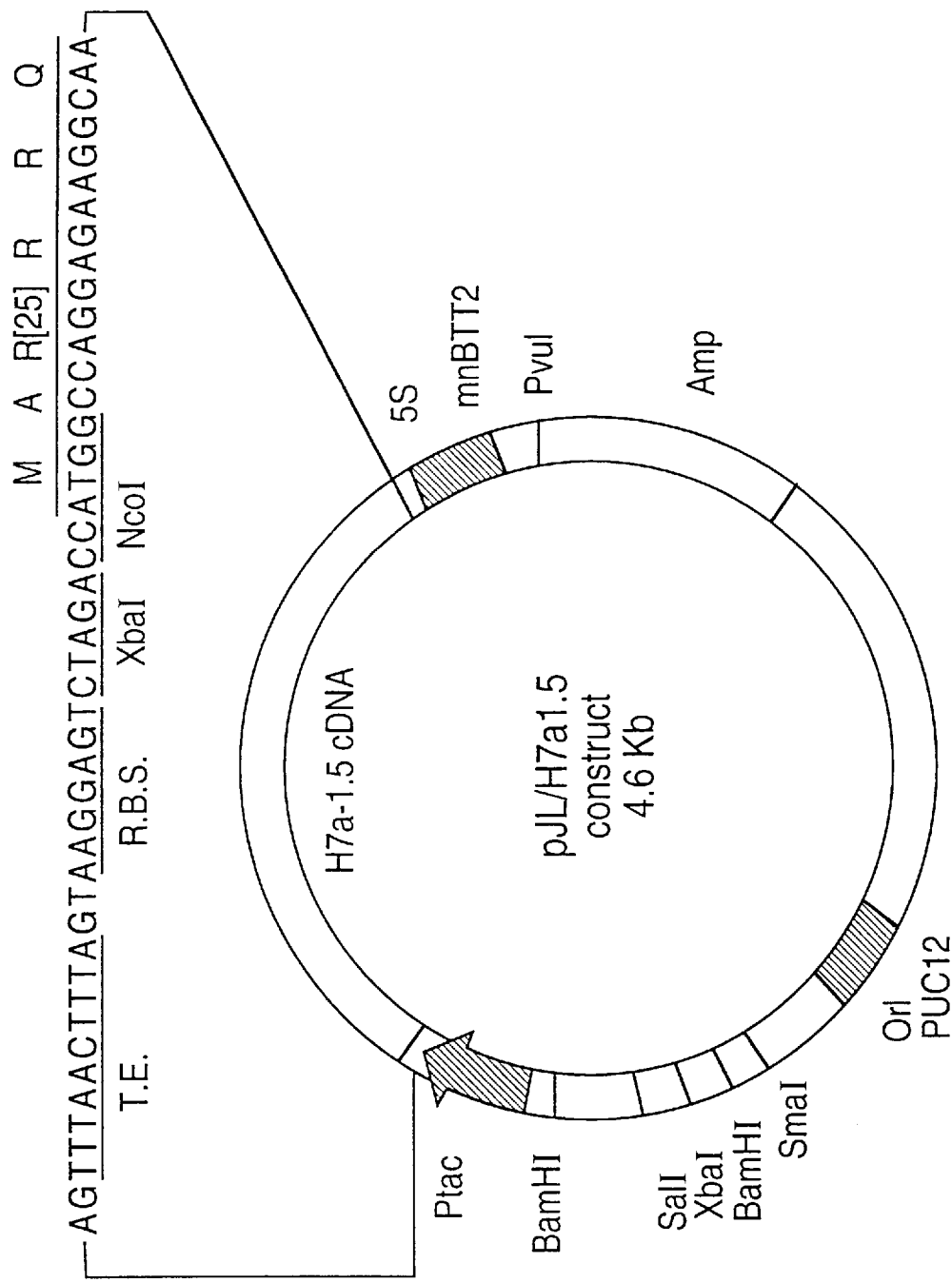
FIG. 9 illustrates a recombinant expression vector construct for truncated human cholesterol 7α-hydroxylase cDNA. Nucleotides 1–46 of SEQ ID NO:4 are also shown in this Figure. The PCR-generated cDNA, H7α1.5, was inserted in an NcoI digested expression vector pJL, as described in Example 1. Abbreviations are as follows: Transcription enhancer (T.E.), ribosome binding site (R.B.S.), Xba I and NcoI (restriction enzyme sites), M (methionine), A (alanine), R[25] (arginine, residue 25 of full-length protein); G (glutamine). In the vector, restriction enzyme sites, the ampicillin resistance gene (Amp), the origin of replication of PUC12 (Ori PUC12) and the tac promoter (ptac) are indicated.

Two primers were designed for the generation of a truncated human cholesterol 7α-hydroxylase cDNA by polymerase chain reaction using the full length human clone PHC7F as the template. Karam and Chiang, *Biochem. Biophys. Res. Commun.* 185: 588–95 (1992). The 5'-primer had a sequence (SEQ ID NO: 1) of 5'GCCATGGCCAGGAGAAGGCAAACGGGT-3, which encoded an N-terminus with a sequence (SEQ ID NO:2) of Met-Ala-Arg(25)-Arg(26)-Arg(27)-Glu(28), etc. The 3'-primer had a sequence (SEQ ID NO:3) of GCCATGGCCGTAATATCATCTAG-3,' which was complementary to the cDNA sequence from 1599 to 1612 near the 3'-end of the coding region. The cDNA generated was sequenced to confirm the human sequence (FIG. 8). This cDNA was ligated to the Nco I site (GCCATG) of the pJL plasmid. The recombinant construct, pJL/H7α1.5 (FIG. 9), was then transformed into a battery of bacteria strains.

It was found that the TOPP3 strain of *E. coli* harboring pJL/H7 α 1.5 was capable of expressing truncated human cholesterol 7α-hydroxylase in very high amounts. Bacteria carrying pJL/H7α1.5 were cultured in "Terrific" broth containing 100 μg/ml ampicillin for 6 hours. One (1) mM IPTG was added to induce the production of protein at 30° C. for 15 to 18 hours. Addition of 2 mM δ-aminolevulinic acid in the culture increased the expression level by 100%. About 20 nmol of human cholesterol 7α-hydroxylase were expressed per liter of culture.

EXAMPLE 9

Purification of the Bacterially Expressed Human Cholesterol 7α-Hydroxylases

Culturing the bacteria carrying the recombinant vector encoding truncated human CYP7 was performed by inoculating 8 liters of Terrific broth containing 100 μg/ml ampicillin with a 6-hour culture of TOPP3-pJL/H7α1.5. This culture was grown at 37° C. until the O.D.$_{600}$ reached from about 0.4 to about 0.6, which occurred in about 3 hours. IPTG was added to a final concentration of 1 mM and incubation was carried out at 30° C. for 15 to 18 hours.

After induction, the cultures were harvested by centrifugation at 5,000 rpm for ten minutes at 4° C. The cells were then resuspended in 1/100 volume of buffer A (100 mM potassium phosphate, pH 7.4, 0.5% sodium cholate, 20% glycerol, 0.1 mM EDTA, 0.1 mM DTT and 0.5 mM PMSF). The cells were then lysed in buffer A with 200 μg/ml lysozyme. The supernatant was collected after spinning down the total lysate at 100,000 × g for one (1) hour at 4° C. The pellet was resuspended thoroughly in the same buffer and centrifuged again. Both supernatants were combined and stored on ice overnight after the addition of 100 units of DNaseI. The clear lysate was then applied to an Octylamino Sepharose 4B column (2.6×15 cm). This column was washed and eluted with the same buffer. The eluted fractions were dialyzed against buffer B (10 mM potassium phosphate, pH 7.4, 0.2% sodium cholate, 0.2% Emulgen 911, 0.1 mM EDTA, 0.05 mM DTT, 0.5 mM phenyl methyl sufonyl fluoride (PMSF)), applied to a hydroxyapatite column (2.4×7 cm) and equilibrated with the same buffer. This column was then washed with 200 ml of 10 mM potassium phosphate buffer, then with 150 ml of 50 mM potassium phosphate buffer and then eluted with 300 ml of 100 mM potassium phosphate buffer. These three buffers also contained 20% glycerol, 0.3% sodium cholate, 0.05 mM EDTA, 0.1 mM DTT and 0.5 mM PMSF. The purified sample was brought to 0.2% Emulgen 911 and then dialyzed against 10 mM potassium phosphate buffer, pH 7.4, 20% glycerol, 0.1 mM EDTA, 0.1 mM DTT, 0.5 mM PMSF and 0.2% Emulgen 911 (buffer C). The sample was then applied to a second hydroxylapatite column (0.5×3.0 cm) equilibrated with buffer C and eluted with buffer C but containing 360 mM potassium phosphate. At this stage, the purity of the human cholesterol 7α-hydroxylase was confirmed by SDS-polyacrylamide gel electrophoresis.

EXAMPLE 10

Characterization of the Purified Human Cholesterol 7α-Hydroxylase

The truncated enzyme was purified from recombinant bacteria. Purification methodology is described by Li and Chiang, *J. Biol. Chem.* 266 (29): 19186 (1991), the contents of which are expressly incorporated by reference herein in its entirety. The activity of CYP7, in both the presence and absence of the compound, is measured as described by Chiang, *Meth. Enzym.* 206: 483 (1991), the contents of which is expressly incorporated by reference herein in its entirety.

Purified truncated enzyme was active in the reconstitution of cholesterol 7α-hydroxylase activity in the presence of NADPH-cytochrome P450 reductase and phospholipid (purified CYP7 enzyme (0.1 nmoles), 2 units of NADPH-cytochrome P450 reductase, 40 µg/ml of L-dilauroyl-glyceryl-3-phosphorylcholine, 100 µM cholesterol in 10 µl of 45% Molecusol, 0.015% CHAPS (3-((3-cholamidopropyl) dimethylaminio)-1-propanesulfonate), 0.1M potassium phosphate, pH 7.4, 1 mM EDTA, 5 mM DTT and 0.1% Emulgen 911). The addition of Molecusol, at varying concentrations, stimulated activity by three-fold. The reaction was started by the addition of 1 mM NADPH and proceeded for 20 minutes, at 37° C. Reactions were terminated by adding 0.8% sodium cholate. Products were oxidized by adding 1 unit of cholesterol oxidase and incubated at 37° C. for 10 minutes. The reaction mixture was extracted three (3) times with 6 ml each of petroleum ether and combined extracts were dissolved in 100 µl of acetonitrile:methanol (70:30; v/v) and analyzed on a C18 reverse-phase HPLC column as described previously.Chiang, *Meth. in Enzymol.* 206: 483–91 (1991).

Figure 10:
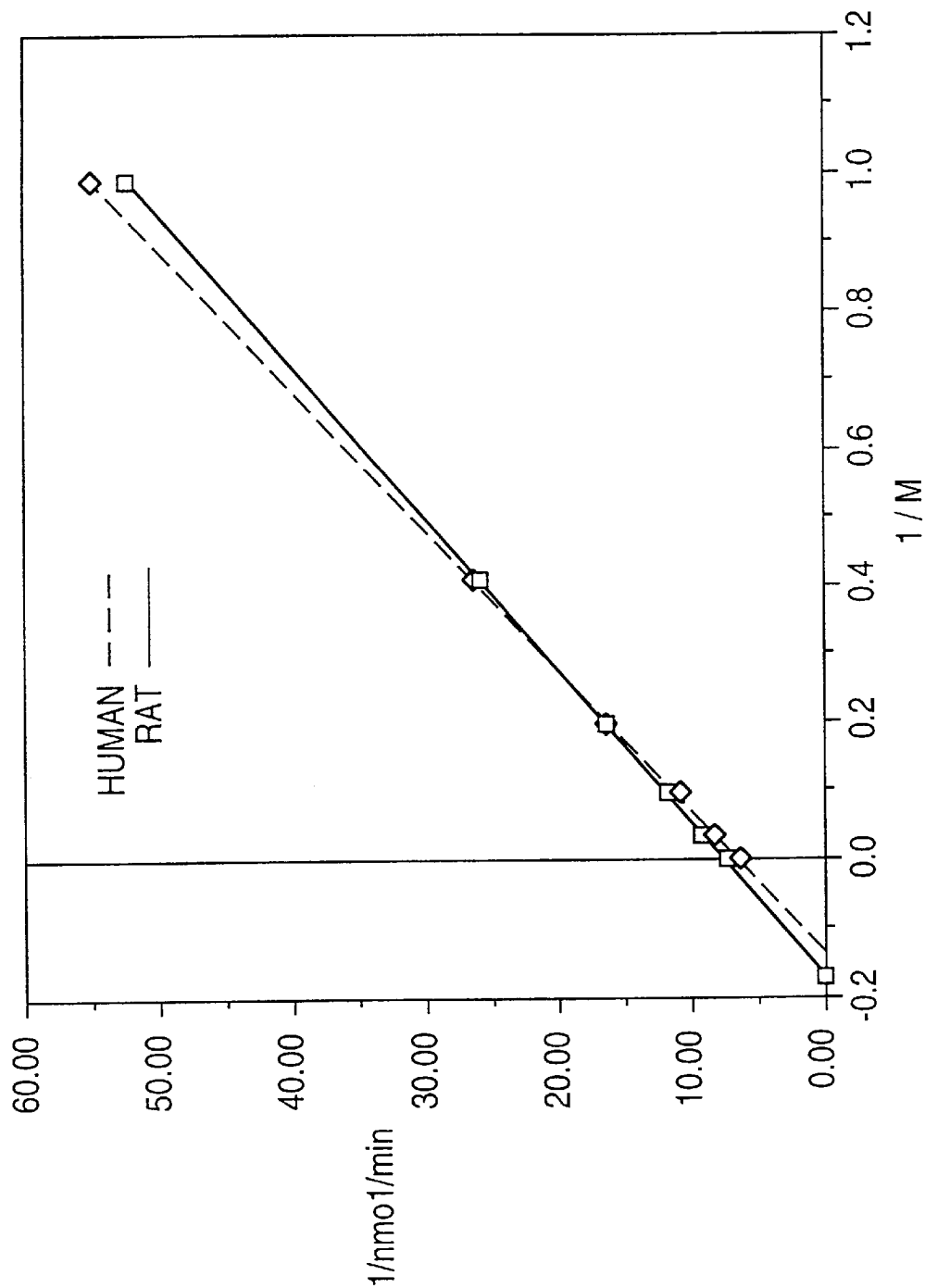
FIG. 10 illustrates a Lineweaver-Burke plot of activities of truncated human and truncated rat cholesterol 7α-hydroxylase in E. coli. Truncated CYP7 activity was measured using a reconstitution assay, such as that described in Example 10, at different concentrations of cholesterol, as indicated. Linear regression was used to draw the line.

The $K_m$ and $V_{max}$ for cholesterol have been determined in comparison with the truncated, bacterially expressed rat CYP7 enzyme (FIG. 10). The $K_m$ for the truncated human enzyme was 5.85 µM and $V_{max}$ was 0.13 nmol/min, which were similar to those of the truncated, bacterially expressed rat enzyme and of intact enzyme isolated from rat liver microsomes. Thus, the isolated truncated human CYP7 enzyme has similar kinetic properties to the truncated rat CYP7 enzyme.

EXAMPLE 11

Assay For Screening Compounds for Ability to Inhibit or Stimulate Non-Truncated CYP7 Enzyme Activity in Human Liver A. Preparation of Antibodies Against the Purified Human Cholesterol 7α-Hydroxylase As mentioned above, an assay system using antibodies raised against purified, truncated human CYP7 is used to screen compounds for their ability to inhibit or stimulate non-truncated CYP7 enzyme activity in human liver. Antibodies to truncated human CYP7 can be produced as follows.

One (1) mg purified truncated CYP7 enzyme was mixed with an equal volume of Freund's adjuvant and 5 mg/ml of heat-killed microbacteria. The emulsified antigen mixtures were injected on the back of New Zealand white rabbits by intradermal injections on multiple sites. After six (6) weeks, 0.5 mg of purified human enzyme was mixed with incomplete adjuvant and used for booster injections to the same rabbits. Six (6) weeks later, blood samples were collected from ear veins and tested for the presence of antibodies by Ouchterlony double diffusion and by immunoblotting as described previously by Chiang et al., *J. Biol. Chem.* 265: 3889–97 (1990), incorporated by reference in its entirety.

For a Western Blot analysis, one (1) µg of purified human CYP7 enzyme was loaded on a 7.5% SDS-polyacrylamide gel, separated polypeptides were electrophoretically transferred to an Immobilon P membrane by a modified procedure reported previously. Chiang et al., supra. (1990). Diluted antisera were reacted with membrane and subsequently reacted with second antibody, anti-rabbit IgG conjugated with alkaline phosphatase, and then stained with nitroblue tetrazolium (NBT) and 5-bromo-4-chloro-3-indolylphosphate (DCIP) as described previously.

B. Assay Using Antibodies Against the Purified Human Cholesterol 7α-Hydroxylase

The specific antibody described above can be used in a screen assay to measure the inhibitory or stimulatory effects of a particular compound on the expression of CYP7 in human liver by a corresponding analysis of the effect on truncated CYP7. To quantitate the amount of expressed truncated enzyme in Western Blot analysis, such as described immediately above, varying concentrations of purified truncated human CYP7 enzyme, from 1 to 10 µgs, are run on adjacent lanes on the 7.5% SDS-polyacrylamide gel to those lanes containing the human CYP7 enzyme from the experimentally treated cells. A stimulation of truncated CYP7 expression is detected by a darker band, relative to control, on the Western blot. If a compound stimulates CYP7 enzyme expression and/or activity, then such an agent or drug could potentially be used to reduce cholesterol in humans. If an agent or drug inhibits CYP7 enzyme expression and/or activity, then such a compound should be used with caution because it potentially could increase serum cholesterol levels in humans.

What is claimed is:

1. A method for screening a compound for its effect on non-truncated human CYP7 enzyme activity, comprising the steps of:
   (a) contacting catalytically active, truncated human CYP7 according to claim 1 with a compound; and
   (b) measuring the catalytic activity of the catalytically active, truncated human CYP7.

2. A method according to claim 1, wherein said compound is a physiological agent derived from the human body.

3. A method according to claim 1, wherein said compound is a physiological agent derived from a source other than the human body.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

G C C A T G G C C A      G G A G A A G G C A      A A C G G G T      2 7

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( D ) TOPOLOGY: linear ( x i ) SEQUENCE DESCRIPTION: SEQ ID NO:2:

Met  Ala  Arg  Arg  Arg  Glu
  1                           5

( 2 ) INFORMATION FOR SEQ ID NO:3:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

GCCATGGCCG  TAATATCATC  TAG                                              23

( 2 ) INFORMATION FOR SEQ ID NO:4:

( i ) SEQUENCE CHARACTERISTICS:
        ( A ) LENGTH: 1524 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:4:

```
AGTTTAACTT  TAGTAAGGAG  TCTAGACCAT  GGCCAGGAGA  AGGCAAACGG  GTGAACCACC     60
TCTAGAGAAT  GGATTAATTC  CATACCTGGG  CTGTGCTCTG  CAATTTGGTG  CCAATCCTCT    120
TGAGTTCCTC  AGAGCAAATC  AAAGGAAACA  TGGTCATGTT  TTTACCTGCA  AACTAATGGG    180
AAAATATGTC  CATTTCATCA  CAAATCCCTT  GTCATACCAT  AAGGTGTTGT  GCCACGGAAA    240
ATATTTTGAT  TGGAAAAAAT  TTCACTTTGC  TACTTCTGCG  AAGGCATTTG  GCACAGAAG     300
CATTGACCCG  ATGGATGGAA  ATACCACTGA  AAACATAAAC  GACACTTTCA  TCAAAACCCT    360
GCAGGGCCAT  GCCTTGAATT  CCCTCACGGA  AAGCATGATG  GAAAACCTCC  AACGTATCAT    420
GAGACCTCCA  GTCTCCTCTA  ACTCAAAGAC  CGCTGCCTGG  GTGACAGAAG  GGATGTATTC    480
TTTCTGCTAC  CGAGTGATGT  TTGAAGCTGG  GTATTAACT   ATCTTTGGCA  GAGATCTTAC    540
AAGGCGGGAC  ACACAGAAAG  CACATATTCT  AAACAATCTT  GACAACTTCA  AGCAATTCGA    600
CAAAGTCTTT  CCAGCCCTGG  TAGCAGGCCT  CCCCATTCAC  ATGTTCAGGA  CTGCGCACAA    660
TGCCCGGGAG  AAACTGGCAG  AGAGCTTGAG  GCACGAGAAC  CTCCAAAAGA  GGGAAAGCAT    720
CTCAGAACTG  ATCAGCCTGC  GCATGTTTCT  CAATGACACT  TTGTCCACCT  TGATGATCT    780
GGAGAAGGCC  AAGACACACC  TCGTGGTCCT  CTGGGCATCG  CAAGCAAACA  CCATTCCAGC    840
GACTTTCTGG  AGTTTATTTC  AAATGATTAG  GAACCCAGAA  GCAATGAAAG  CAGCTACTGA    900
AGAAGTGAAA  AGAACATTAG  AGAATGCTGG  TCAAAAAGTC  AGCTTGGAAG  GCAATCCTAT    960
TTGTTTGAGT  CAAGCAGAAC  TGAATGACCT  GCCAGTATTA  GATAGTATAA  TCAAGGAATC   1020
GCTGAGGCTT  TCCAGTGCCT  CCCTCAACAT  CCGGACAGCT  AAGGAGGATT  TCACTTTGCA   1080
CCTTGAGGAC  GGTTCCTACA  ACATCCGAAA  AGATGACATC  ATAGCTCTTT  ACCCACAGTT   1140
AATGCACTTA  GATCCAGAAA  TCTACCCAGA  CCCTTTGACT  TTTAAATATG  ATAGGTATCT   1200
TGATGAAAAC  GGGAAGACAA  AGACTACCTT  CTATTGTAAT  GGACTCAAGT  TAAAGTATTA   1260
```

```
CTACATGCCC   TTTGGATCGG   GAGCTACAAT   ATGTCCTGGA   AGATTGTTCG   CTATCCACGA       1320

AATCAAGCAA   TTTTTGATTC   TGATGCTTTC   TTATTTGAA    TTGGAGCTTA   TAGAGGGCCA       1380

AGCTAAATGT   CCACCTTTGG   ACCAGTCCCG   GGCAGGCTTG   GGCATTTTGC   CGCCATTGAA       1440

TGATATTGAA   TTTAAATATA   AATTCAAGCA   TTTGTGAATA   CATGGCTGGA   ATAAGAGGAC       1500

ACTAGATGAT   ATTACGGCCA   TGGC                                                    1524
```

( 2 ) INFORMATION FOR SEQ ID NO:5:

( i ) SEQUENCE CHARACTERISTICS:
        ( A ) LENGTH: 482 amino acids
        ( B ) TYPE: amino acid
        ( D ) TOPOLOGY: linear ( x i ) SEQUENCE DESCRIPTION: SEQ ID NO:5:

```
Met  Ala  Arg  Arg  Arg  Gln  Thr  Gly  Glu  Pro  Pro  Leu  Glu  Asn  Gly  Leu
 1              5                        10                       15

Ile  Pro  Tyr  Leu  Gly  Cys  Ala  Leu  Gln  Phe  Gly  Ala  Asn  Pro  Leu  Glu
              20                       25                       30

Phe  Leu  Arg  Ala  Asn  Gln  Arg  Lys  His  Gly  His  Val  Phe  Thr  Cys  Lys
              35                       40                       45

Leu  Met  Gly  Lys  Tyr  Val  His  Phe  Ile  Thr  Asn  Pro  Leu  Ser  Tyr  His
      50                       55                       60

Lys  Val  Leu  Cys  His  Gly  Lys  Tyr  Phe  Asp  Trp  Lys  Lys  Phe  His  Phe
 65                       70                       75                       80

Ala  Thr  Ser  Ala  Lys  Ala  Phe  Gly  His  Arg  Ser  Ile  Asp  Pro  Met  Asp
                   85                       90                       95

Gly  Asn  Thr  Thr  Glu  Asn  Ile  Asn  Asp  Thr  Phe  Ile  Lys  Thr  Leu  Gln
              100                      105                      110

Gly  His  Ala  Leu  Asn  Ser  Leu  Thr  Glu  Ser  Met  Met  Glu  Asn  Leu  Gln
              115                      120                      125

Arg  Ile  Met  Arg  Pro  Pro  Val  Ser  Ser  Asn  Ser  Lys  Thr  Ala  Ala  Trp
     130                      135                      140

Val  Thr  Glu  Gly  Met  Tyr  Ser  Phe  Cys  Tyr  Arg  Val  Met  Phe  Glu  Ala
145                      150                      155                      160

Gly  Tyr  Leu  Thr  Ile  Phe  Gly  Arg  Asp  Leu  Thr  Arg  Arg  Asp  Thr  Gln
                   165                      170                      175

Lys  Ala  His  Ile  Leu  Asn  Asn  Leu  Asp  Asn  Phe  Lys  Gln  Phe  Asp  Lys
              180                      185                      190

Val  Phe  Pro  Ala  Leu  Val  Ala  Gly  Leu  Pro  Ile  His  Met  Phe  Arg  Thr
              195                      200                      205

Ala  His  Asn  Ala  Arg  Glu  Lys  Leu  Ala  Glu  Ser  Leu  Arg  His  Glu  Asn
     210                      215                      220

Leu  Gln  Lys  Arg  Glu  Ser  Ile  Ser  Glu  Leu  Ile  Ser  Leu  Arg  Met  Phe
225                      230                      235                      240

Leu  Asn  Asp  Thr  Leu  Ser  Thr  Phe  Asp  Asp  Leu  Glu  Lys  Ala  Lys  Thr
                   245                      250                      255

His  Leu  Val  Val  Leu  Trp  Ala  Ser  Gln  Ala  Asn  Thr  Ile  Pro  Ala  Thr
                   260                      265                      270

Phe  Trp  Ser  Leu  Phe  Gln  Met  Ile  Arg  Asn  Pro  Glu  Ala  Met  Lys  Ala
          275                      280                      285

Ala  Thr  Glu  Glu  Val  Lys  Arg  Thr  Leu  Glu  Asn  Ala  Gly  Gln  Lys  Val
     290                      295                      300

Ser  Leu  Glu  Gly  Asn  Pro  Ile  Cys  Leu  Ser  Gln  Ala  Glu  Leu  Asn  Asp
305                      310                      315                      320
```

| | | | | | | | | | | | | | | | |
|---|---|---|---|---|---|---|---|---|---|---|---|---|---|---|---|
|Leu|Pro|Val|Leu|Asp|Ser|Ile|Ile|Lys|Glu|Ser|Leu|Arg|Leu|Ser|Ser|
| | | | |325| | | |330| | | |  |335| | |

| | | | | | | | | | | | | | | | |
|---|---|---|---|---|---|---|---|---|---|---|---|---|---|---|---|
|Ala|Ser|Leu|Asn|Ile|Arg|Thr|Ala|Lys|Glu|Asp|Phe|Thr|Leu|His|Leu|
| | | |340| | | |345| | | | |350| | | |

| | | | | | | | | | | | | | | | |
|---|---|---|---|---|---|---|---|---|---|---|---|---|---|---|---|
|Glu|Asp|Gly|Ser|Tyr|Asn|Ile|Arg|Lys|Asp|Asp|Ile|Ile|Ala|Leu|Tyr|
| | |355| | | | |360| | | | |365| | | |

| | | | | | | | | | | | | | | | |
|---|---|---|---|---|---|---|---|---|---|---|---|---|---|---|---|
|Pro|Gln|Leu|Met|His|Leu|Asp|Pro|Glu|Ile|Tyr|Pro|Asp|Pro|Leu|Thr|
| |370| | | | |375| | | | |380| | | | |

| | | | | | | | | | | | | | | | |
|---|---|---|---|---|---|---|---|---|---|---|---|---|---|---|---|
|Phe|Lys|Tyr|Asp|Arg|Tyr|Leu|Asp|Glu|Asn|Gly|Lys|Thr|Lys|Thr|Thr|
|385| | | | |390| | | | |395| | | | |400|

| | | | | | | | | | | | | | | | |
|---|---|---|---|---|---|---|---|---|---|---|---|---|---|---|---|
|Phe|Tyr|Cys|Asn|Gly|Leu|Lys|Leu|Lys|Tyr|Tyr|Tyr|Met|Pro|Phe|Gly|
| | | | |405| | | |410| | | | |415| | |

| | | | | | | | | | | | | | | | |
|---|---|---|---|---|---|---|---|---|---|---|---|---|---|---|---|
|Ser|Gly|Ala|Thr|Ile|Cys|Pro|Gly|Arg|Leu|Phe|Ala|Ile|His|Glu|Ile|
| | | |420| | | | |425| | | | |430| | |

| | | | | | | | | | | | | | | | |
|---|---|---|---|---|---|---|---|---|---|---|---|---|---|---|---|
|Lys|Gln|Phe|Leu|Ile|Leu|Met|Leu|Ser|Tyr|Phe|Glu|Leu|Glu|Leu|Ile|
| | |435| | | | |440| | | | |445| | | |

| | | | | | | | | | | | | | | | |
|---|---|---|---|---|---|---|---|---|---|---|---|---|---|---|---|
|Glu|Gly|Gln|Ala|Lys|Cys|Pro|Pro|Leu|Asp|Gln|Ser|Arg|Ala|Gly|Leu|
| |450| | | | |455| | | | |460| | | | |

| | | | | | | | | | | | | | | | |
|---|---|---|---|---|---|---|---|---|---|---|---|---|---|---|---|
|Gly|Ile|Leu|Pro|Pro|Leu|Asn|Asp|Ile|Glu|Phe|Lys|Tyr|Lys|Phe|Lys|
|465| | | | |470| | | | |475| | | | |480|

| | |
|---|---|
|His|Leu|

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

TACCGCTCGA GTGATTAGAA AGGGAAGGAT      30

(2) INFORMATION FOR SEQ ID NO:7:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

CAAGAATGAT AGATAAAAT      19

(2) INFORMATION FOR SEQ ID NO:8:

(i) SEQUENCE CHARACTERISTICS:
        (A) LENGTH: 504 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

| | | | | | | | | | | | | | | | |
|---|---|---|---|---|---|---|---|---|---|---|---|---|---|---|---|
|Met|Met|Thr|Thr|Ser|Leu|Ile|Trp|Gly|Ile|Ala|Ile|Ala|Ala|Cys|Cys|
|1| | | |5| | | |10| | | | |15| | |

| | | | | | | | | | | | | | | | |
|---|---|---|---|---|---|---|---|---|---|---|---|---|---|---|---|
|Cys|Leu|Trp|Leu|Ile|Leu|Gly|Ile|Arg|Arg|Arg|Gln|Thr|Gly|Glu|Pro|
| | | |20| | | |25| | | | |30| | | |

```
Pro  Leu  Glu  Asn  Gly  Leu  Ile  Pro  Tyr  Leu  Gly  Cys  Ala  Leu  Gln  Phe
          35                      40                     45

Gly  Ala  Asn  Pro  Leu  Glu  Phe  Leu  Arg  Ala  Asn  Gln  Arg  Lys  His  Gly
     50                      55                      60

His  Val  Phe  Thr  Cys  Lys  Leu  Met  Gly  Lys  Tyr  Val  His  Phe  Ile  Thr
65                       70                      75                           80

Asn  Pro  Leu  Ser  Tyr  His  Lys  Val  Leu  Cys  His  Gly  Lys  Tyr  Phe  Asp
                    85                      90                      95

Trp  Lys  Lys  Phe  His  Phe  Ala  Thr  Ser  Ala  Lys  Ala  Phe  Gly  His  Arg
               100                      105                     110

Ser  Ile  Asp  Pro  Met  Asp  Gly  Asn  Thr  Thr  Glu  Asn  Ile  Asn  Asp  Thr
          115                     120                     125

Phe  Ile  Lys  Thr  Leu  Gln  Gly  His  Ala  Leu  Asn  Ser  Leu  Thr  Glu  Ser
     130                     135                     140

Met  Met  Glu  Asn  Leu  Gln  Arg  Ile  Met  Arg  Pro  Pro  Val  Ser  Ser  Asn
145                      150                     155                          160

Ser  Lys  Thr  Ala  Ala  Trp  Val  Thr  Glu  Gly  Met  Tyr  Ser  Phe  Cys  Tyr
                    165                     170                     175

Arg  Val  Met  Phe  Glu  Ala  Gly  Tyr  Leu  Thr  Ile  Phe  Gly  Arg  Asp  Leu
               180                     185                     190

Thr  Arg  Arg  Asp  Thr  Gln  Lys  Ala  His  Ile  Leu  Asn  Asn  Leu  Asp  Asn
          195                     200                     205

Phe  Lys  Gln  Phe  Asp  Lys  Val  Phe  Pro  Ala  Leu  Val  Ala  Gly  Leu  Pro
     210                     215                     220

Ile  His  Met  Phe  Arg  Thr  Ala  His  Asn  Ala  Arg  Glu  Lys  Leu  Ala  Glu
225                      230                     235                          240

Ser  Leu  Arg  His  Glu  Asn  Leu  Gln  Lys  Arg  Glu  Ser  Ile  Ser  Glu  Leu
                    245                     250                     255

Ile  Ser  Leu  Arg  Met  Phe  Leu  Asn  Asp  Thr  Leu  Ser  Thr  Phe  Asp  Asp
               260                     265                     270

Leu  Glu  Lys  Ala  Lys  Thr  His  Leu  Val  Val  Leu  Trp  Ala  Ser  Gln  Ala
          275                     280                     285

Asn  Thr  Ile  Pro  Ala  Thr  Phe  Trp  Ser  Leu  Phe  Gln  Met  Ile  Arg  Asn
     290                     295                     300

Pro  Glu  Ala  Met  Lys  Ala  Ala  Thr  Glu  Glu  Val  Lys  Arg  Thr  Leu  Glu
305                      310                     315                          320

Asn  Ala  Gly  Gln  Lys  Val  Ser  Leu  Glu  Gly  Asn  Pro  Ile  Cys  Leu  Ser
                    325                     330                     335

Gln  Ala  Glu  Leu  Asn  Asp  Leu  Pro  Val  Leu  Asp  Ser  Ile  Ile  Lys  Glu
               340                     345                     350

Ser  Leu  Arg  Leu  Ser  Ser  Ala  Ser  Leu  Asn  Ile  Arg  Thr  Ala  Lys  Glu
          355                     360                     365

Asp  Phe  Thr  Leu  His  Leu  Glu  Asp  Gly  Ser  Tyr  Asn  Ile  Arg  Lys  Asp
     370                     375                     380

Asp  Ile  Ile  Ala  Leu  Tyr  Pro  Gln  Leu  Met  His  Leu  Asp  Pro  Glu  Ile
385                      390                     395                          400

Tyr  Pro  Asp  Pro  Leu  Thr  Phe  Lys  Tyr  Asp  Arg  Tyr  Leu  Asp  Glu  Asn
                    405                     410                     415

Gly  Lys  Thr  Lys  Thr  Thr  Phe  Tyr  Cys  Asn  Gly  Leu  Lys  Leu  Lys  Tyr
               420                     425                     430

Tyr  Tyr  Met  Pro  Phe  Gly  Ser  Gly  Ala  Thr  Ile  Cys  Pro  Gly  Arg  Leu
          435                     440                     445

Phe  Ala  Ile  His  Glu  Ile  Lys  Gln  Phe  Leu  Ile  Leu  Met  Leu  Ser  Tyr
```

|   |   |   |   | 450 |   |   |   | 455 |   |   |   | 460 |   |
|---|---|---|---|---|---|---|---|---|---|---|---|---|---|
| Phe | Glu | Leu | Glu | Leu | Ile | Glu | Gly | Gln | Ala | Lys | Cys | Pro | Pro | Leu | Asp |
| 465 | | | | | 470 | | | | 475 | | | | 480 |
| Gln | Ser | Arg | Ala | Gly | Leu | Gly | Ile | Leu | Pro | Pro | Leu | Asn | Asp | Ile | Glu |
| | | | | 485 | | | | | 490 | | | | 495 |
| Phe | Lys | Tyr | Lys | Phe | Lys | His | Leu |
| | | | 500 |

( 2 ) INFORMATION FOR SEQ ID NO:9:

( i ) SEQUENCE CHARACTERISTICS:
        ( A ) LENGTH: 5537 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

| | | | | | |
|---|---|---|---|---|---|
| TTTTTGGTTA | TCTTTTCAGC | CGTGCCCCAC | TCTACTGGTA | CCAGTTTACT | GTATTAGTCG | 60 |
| ATTTTCATGC | TGCTGATAAA | GACATACCTG | AAACTGGACA | ATTTACAAAA | GAAAGAGGTT | 120 |
| TATTGGACTT | ACAATTCTAC | ATCACTTGGG | AGGCCTCACA | ATCATGATGG | AAGGAGAAAG | 180 |
| GCACATCTCA | CATGGCAGCA | GACAAGAAAA | GAGCTTGTGC | AGGGAAACTC | CTCTTTTTAA | 240 |
| AACCATCAGA | TCTCATGAAA | TTTATTCATT | ATCATGACAA | TAGCACAGGA | AAGAACTGCA | 300 |
| CCCATAATTC | AGTCACCTCC | TACCAGGTTC | CTCCCACAAC | ACGTGAGAAT | TCAAGATGAG | 360 |
| ATTTGGATGG | GGACACAGCC | AAACCATGTC | ACTACCAT | GCCTGACTTC | CTTTCCATTT | 420 |
| TTGTATATTT | GCTTGTTCTT | CATTTGCCCG | AGAAGTAACT | CTAAAGGGCT | GTATTATTTG | 480 |
| GATATTAGAT | TGGCATTTTA | TCTGACTGGG | ATATCTTGCT | GTGATTGTCC | ATGTATAAGA | 540 |
| TCAGCTTTTC | TATAAGCCAT | ATTTTAAAA | AGATATATTA | ATTTTTAAA | AATCCACCTG | 600 |
| TCTAAATAAA | TGCACAAAGC | CCCCCAAAAA | CCTAGATTCT | AAGAAAAATC | TATGTACTGC | 660 |
| CATACAATGA | TTGATATTAA | TATTTATGGT | GATAAATTAC | ACACAAAAA | TGTGTGATCT | 720 |
| CTGTTTAAAC | AGGCAAAAAC | AAAAAACACA | TGAAATAAAT | CTATGGCATC | TATAGCCAAA | 780 |
| ACTGGAAACA | ACCCACATAT | CCATCAATAG | GAAATCAGTT | AAATAAATTA | TAGTACATTT | 840 |
| ATCCAATGGA | AGATTAAGCA | CATATTCAAT | ATAATTATTT | ATACACACAT | ATAGATACAC | 900 |
| ACATGTATAA | ATATAGAGAA | TACTGTGGGT | GTATGTGTGT | GTGTGTTTAT | ATACATATAT | 960 |
| ATACACACAC | AGTACTGTTG | CCTACCTTCT | TTTGTCTTAA | TTCTGTGAAC | TCTCATTCAC | 1020 |
| TCTGCTTCAG | TAGGATACCT | CCTTCTTTTT | GGTTCTTAGA | CTCACCAAGT | TGATCCTTGA | 1080 |
| CTCAAGACAT | TGCATTTGCT | GCTTCCTCTT | CCTGGAATAT | CCTTCCTTCT | GATATTCACA | 1140 |
| TGAGTAGTCT | CTTCTTGTCA | TTCAGATCTC | AAATGTCACA | ATTTCAGAGA | GCCCATCTCT | 1200 |
| GATCATCATA | TCTAAAGTTG | TCCTCATTCC | CCCATAGCTT | TCTATACCAT | GTTTTATTTT | 1260 |
| TTTCATAACA | TGTATTTTAT | TACTCCTTTC | TCCATTGGAA | TAGAATCTCC | ATTAGATTAG | 1320 |
| GAAATCTGCC | TATCTTATTA | ATGCCTGCAA | CTGGAATACT | TTTGAAGAGT | TCTTGGCACG | 1380 |
| TAATAAATAC | TCAACTAATA | TTTTTGTGTA | CACAGAAATA | AAGTTTGGAA | GAACAGATGC | 1440 |
| CAAATTGTTA | CTAGTGGTTA | CTTCTGAGTA | AAGGAGTAGC | ATGGTAGGTA | AATTATTAAT | 1500 |
| AGATGTTCAC | TTTCCACCAA | GATATGTTTT | AGTTAGTCTT | AACTTACTTG | AAATGAAATT | 1560 |
| TATTACTTTA | ATAATTAGAA | ACATTGATAA | ACATTTTAGT | CACAAGAATG | ATAGATAAAA | 1620 |
| TTTTGATGCT | TCCAATAAGT | TATATTTATC | TAGAGGATGC | ACTTATGTAG | AATACTCTCT | 1680 |

| | | | | | | |
|---|---|---|---|---|---|---|
| TGAGGATGTT | AGGTGAGTAA | CATGTTACTA | TATGTAGTAA | AATATCTATG | ATTTTATAAA | 1740 |
| AGCACTGAAA | CATGAAGCAG | CAGAAATGTT | TTTCCCAGTT | CTCTTTCCTC | TGAACTTGAT | 1800 |
| CACCGTCTCT | CTGGCAAAGC | ACCTAAATTA | ATTCTTCTTT | AAAAGTTAAC | AAGACCAAAT | 1860 |
| TATAAGCTTG | ATGAATAACT | CATTCTTATC | TTTCTTTAAA | TGATTATAGT | TTATGTATTT | 1920 |
| ATTAGCTATG | CCCATCTTAA | ACAGGTTTAT | TTGTTCTTTT | TACACATACC | AAACTCTTAA | 1980 |
| TATTAGCTGT | TGTCCCCAGG | TCCGAATGTT | AAGTCAACAT | ATATTTGAGA | GACCTTCAAC | 2040 |
| TTATCAAGTA | TTGCAGGTCT | CTGATTGCTT | TGGAACCACT | TCTGATACCT | GTGGACTTAG | 2100 |
| TTCAAGGCCA | GTTACTACCA | CTTTTTTTTT | TCTAATAGAA | TGAACAAATG | GCTAATTGTT | 2160 |
| TGCTTTGTCA | ACCAAGCTCA | AGTTAATGGA | TCTGGATACT | ATGTATATAA | AAAGCCTAGC | 2220 |
| TTGAGTCTCT | TTTCAGTGGC | ATCCTTCCCT | TTCTAATCAG | AGATTTTCTT | CCTCAGAGAT | 2280 |
| TTTGGCCTAG | ATTTGCAAAA | TGATGACCAC | ATCTTTGATT | TGGGGGATTG | CTATAGCAGC | 2340 |
| ATGCTGTTGT | CTATGGCTTA | TTCTTGGAAT | TAGGAGAAGG | TAAGTAATGT | TTTATCTTTA | 2400 |
| AATTGCTCTT | TGATTCATCC | ATTTAATTTT | TTTACCTTCA | TTTTTATACA | GTAAATTTGG | 2460 |
| TTTTCTATAC | TTACACATAT | TAGCATTATC | TTCCTTATGT | TTTAAATGAA | AAATTTGATT | 2520 |
| TGAATTTTTA | AAGTAATATC | TTTTTTACTA | TATCTCACAA | GACATATGAC | AGCTTCCCTT | 2580 |
| TTTAGTATTG | GCATATACCG | ATGGTAATAT | ATAAATGTAT | ATTGGTGTTA | AACATAACTG | 2640 |
| ACAGAAATTG | TATAAGGTCT | CTATGTACAT | TTATATGTGT | ATCTAAAGAG | GAAGCCCAGA | 2700 |
| TTAGTAAGGA | TACAAGTAGC | AAGTGGGAAT | CTACAATGGA | AAGGATTGCT | TTCTCTCACA | 2760 |
| TGGCTTCAAT | AGATACTCTT | GCTTAAATAA | ATGTTCTCTT | TTAAGCTCAT | TCTTGTGCAT | 2820 |
| CGCATAGACT | CAGCCTAAGC | CTGAACAAGA | GCATAGAGCC | TGAGCTGATC | ATTCTATTAC | 2880 |
| TGTTTTTAAA | TAAATGTTAA | TCAACTGTGG | TGAATTGGGA | AAGTTTGCTG | AGTGTATGTG | 2940 |
| ACATCGATTT | CATTTATTTA | CAACTGGTTC | AAGAATGCAA | GAAAACAAA | TACAGTCAGA | 3000 |
| TCCAGAACCA | TAGTTTATTT | AACTTCTAAT | TGGCTCAAGG | AGTAATTGTG | GGGAGGCATA | 3060 |
| TAGATATTCT | CTGCTATGTC | AATCTCAAAA | AGAGAAAATA | ACCCTAACCA | TCTTTCAGCT | 3120 |
| TTGTAGATTG | CTATGTGTTT | TCTGCCTTTG | CAGTTTCTTT | CAGGCCTGAT | AGTTTTTACT | 3180 |
| TTTAATTAAA | CTACTTATCT | TCAAACTAAG | AAAAGAAAGG | TAATTACTTT | ATACTGTATT | 3240 |
| ATTCTATCAA | GAGGTACAGA | AGTTTATGTT | GGAAAATAAG | TTTACATGTT | CTAATAAAAA | 3300 |
| CATTTTAAAG | GAGCACTGAA | TTACAATAGA | TGATTCCGTC | AGTGTTATC | TTACTCAATT | 3360 |
| TCATTTTATA | ATAAGCTGAT | TTCTCACATG | AGATTCTTCT | TCTCTGAAAC | CATCCTTATA | 3420 |
| GAATATAATA | TAGATATCTT | TAAACTAGGA | ATATTTTCAA | AACCTCAGTT | CTGAAATCCT | 3480 |
| CCCTTATTCA | GTGATCTGTG | TCTTTAAAGA | AAATAATCAA | AAGAAACATT | TGAGATATT | 3540 |
| TAGAAAAATG | ATGCTTAGCA | AAGTGATAAA | CACTAGAATG | TAGTTTTGTT | TCCGCACTGA | 3600 |
| CAACAAGAAT | CTTGTTGGTC | TTGTAAATCC | TTTTGCCTGT | ATCACTGGGA | AAAGTGATGA | 3660 |
| GCACATAGTA | GACGGGTGCT | TGTTGAATGT | GTATATGGAC | GGATGCATGA | ATGGATGGAT | 3720 |
| TTAGTAATCC | TTTCCACCAA | CATATCATGT | TACTAGGTTA | ATATAACCTA | TTACTGTAGT | 3780 |
| AAAAGAGCAG | GGCCCATCCA | ACAAAGAAA | TATCTATAAA | CTATAGGGTT | TCAAAGTTTG | 3840 |
| AAGTCAGTGG | GAAAAATTTT | AAAACCTGAT | GTAAGTAAAA | ACCCAAAACT | GTAATCATCC | 3900 |
| ATGTCTATCA | TACACTTGTG | TCTGACAGGC | AAACGGGTGA | ACCACCTCTA | GAGAATGGAT | 3960 |
| TAATTCCATA | CCTGGGCTGT | GCTCTGCAAT | TTGGTGCCAA | TCCTCTTGAG | TTCCTCAGAG | 4020 |
| CAAATCAAAG | GAAACATGGT | CATGTTTTTA | CCTGCAAACT | AATGGGAAAA | TATGTCCATT | 4080 |

| | | | | | | |
|---|---|---|---|---|---|---|
| TCATCACAAA | TCCCTTGTCA | TACCATAAGG | TGTTGTGCCA | CGGAAAATAT | TTTGATTGGA | 4140 |
| AAAAATTTCA | CTTTGCTACT | TCTGCGAAGG | TAAGCAGTTT | TACATTTATA | TACCATTCTG | 4200 |
| TTTGTCTTCT | ACCTTTTTAT | GTGCTTGTCT | ATTTAGAAAT | TTTGATGTAC | TTAGATTTTA | 4260 |
| TGATAAAGGT | GTTGAAGAGA | GTTATCCTTA | TGTGGAGATT | CTTAGAAACA | TAAATAAATT | 4320 |
| ATACGTAGCT | TCTTAGTAAT | AATCATTTAG | AAAGTCAAAA | TAGGTATAGA | TTTCCGTCAT | 4380 |
| TTGCTTTGCA | CGAGCTAATG | AGGGTGAAAT | ACAGATTAAA | TGCTCTACTG | AGACAGGTGG | 4440 |
| CACTGTACGA | ATAAGATAGA | TTAAAATTCA | TCACATCAGC | AATGTCTATG | CAGAGCGAAG | 4500 |
| TGACGGAAAC | CTAACATTCA | GCAGTTGTCT | CACCACACTT | GTGCCACACA | GTGTTTCATT | 4560 |
| TTGATAAGGA | ATTGGCAAGA | TATTTTAACA | TCATTTAGAT | GTAATAAAAG | AAGATCTGTT | 4620 |
| ACTGAGAAAA | AAAACCAATA | ACTACTTACT | TACTGCAAAT | AAATATTAGC | TTTGGTCTTT | 4680 |
| GTGACTAAGT | AGCTTAAAGT | TTGGTTAAAA | TACATCTACA | GCTGGACACA | ATGGAACACA | 4740 |
| CCTGTAGTCC | CTGCTATTTG | AGAGGCTGAG | GCAGGAGGAT | CGCTTGAGTC | CAGGAGTTTG | 4800 |
| AGGCTGCAGT | GAGCTATCAT | TGTGTCACTG | CACTCCAGCC | TGGGTGACAA | TGTGAGACCC | 4860 |
| CATCTCTAAA | AGAAAAAGAA | AAAGAAATCT | ACAAATAATA | TAAAAGATAA | CTAATGATTT | 4920 |
| TAAAACATTA | TCAATTAGTT | TATGTGCAAT | AGCTGTAAAT | AAGTGCAGTA | GCATAAGAAA | 4980 |
| TAAGACATAG | ATGACTTGAG | TGATCCAGGG | GAGTGCCACT | GAAGTTGGCT | TTAAAGGAAA | 5040 |
| GGTACAGTTT | GGTCATTTAT | TTGTAAAGTG | CTATGAACTT | GTACAAGGGA | AAGCCAATTT | 5100 |
| CCCGTGTTTA | CCAAGTAAGG | AACTATGAAA | GTATCTAATC | CGTTTTCAG | TCATTTACTA | 5160 |
| TGACTAGGTC | AGGTTTAACT | TCTTTTTCTG | CATGTTTTAT | TTGCTATCAG | GCATTTGGGC | 5220 |
| ACAGAAGCAT | TGACCCGATG | GATGGAAATA | CCACTGAAAA | CATAAACGAC | ACTTTCATCA | 5280 |
| AAACCCTGCA | GGGCCATGCC | TTGAATTCCC | TCACGGAAAG | CATGATGGAA | AACCTCCAAC | 5340 |
| GTATCATGAG | ACCTCCAGTC | TCCTCTAACT | CAAAGACGC | TGCCTGGGTG | ACAGAAGGA | 5400 |
| TGTATTCTTT | CTGCTACCGA | GTGATGTTTG | AAGCTGGGTA | TTTAACTATC | TTTGGCAGAG | 5460 |
| ATCTTACAAG | GCGGGACACA | CAGAAAGCAC | ATATTCTAAA | CAATCTTGAC | AACTTCAAGC | 5520 |
| AATTCGACAA | AGTCTTT | | | | | 5537 |

( 2 ) INFORMATION FOR SEQ ID NO:10:

( i ) SEQUENCE CHARACTERISTICS:
        ( A ) LENGTH: 2575 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

| | | | | | | |
|---|---|---|---|---|---|---|
| GAATTCTACT | CTTTAAAGGG | GTGAATATTA | TGGTACTTGA | ATTTATCTC | AAGAAAAATG | 60 |
| AATAAAAAGT | AACTAAATCA | TTGAAAATAT | CTGATGGCAT | GGGGTTTGTG | GGTAACTGG | 120 |
| CATTCCACAG | TGATTTTCAA | AGGGCTTGTG | CTGTTTTCAT | TTTGCTTTGT | TTTAGTTATG | 180 |
| GAGCCCTTCC | TTGAAACAAA | CTTCATACTA | CAGTCCTCTT | TCATGAAGCA | GAAGAGGGCA | 240 |
| GTGGGCAGAG | CTCTCCTTTG | GCTTTCTCCC | CCACCACAAC | AGGGAGCCCT | GGAGCTCTAG | 300 |
| GAGAGAAAAT | CTGAAATATA | AAGGGCATGC | ATGTGAGCTG | TGGAGTCCCA | GAGCCCTGGG | 360 |
| TTTGCATCCT | AGATCTGCAA | CTCCCGTGAA | TTGAGTTTTG | GAAGTTGCT | GAAACTCTGA | 420 |
| CCTCCTGTTT | TCTCATGGTA | TTGTTGTAAG | GGTTAAATGA | GACAATGTAT | GTGAAGACCC | 480 |
| TGGCCCCACA | GTAGAGGCTC | TGCACACATT | TCAGCGATAC | TTTCCTCATG | TATTTCCAAA | 540 |

-continued

```
AATGTTTTCT CATTTTCTTA AAATGTCAGA AAGAAGACAA CAGAACTTAC TTGCCTTTTA    600
CAACAGAACA AATGGAGCAA GTCAGAGGTC AAGGTGCTAA CATTCTTCAT GGTTCCTCAC    660
CACCTTTTGT TCTGTTAGCC TATAGGGAAA AGTCTTCTTT CTCATCTCAT TATCTGCAGG    720
GGAAAATAGT ACTTCAGCAA GTGATCCAGT TGAAGAACAT CTCCAGGGCC ATTAACATAC    780
AGAGGTTTGT TCTACTCTCT CTGTGCTCCA TGTCTAAGAA CCTCAGCCTT CCTCCTAGGA    840
GCTAGGGAAA GTCAGGAAAG TGAAAATAGT ACCCAGCTA ATGAACTGCC CTGTGCTGGC    900
CTGAGAAGAC AAGACCAGCT TCCTCAATGG CTCAAGATTT GGTTTCCTTC AATATGTCCT    960
TTTGGAAATA TGTCCATGAC ATCGGAGAGA TAAAGGAGC CAGGATTGCT CACATTCAGG    1020
AAAAAGCTC CACTATCTTT CTCTCTCTCC CTCTTTCTCT CCCTCCCCCT GACTGCCCTC    1080
TTCTCTATCT CTCTCTCTCC CTGAGCTGGC AAGGTTAATT GGTCGCAGAA AGCCGAAGAA    1140
ACAAGTGGGC CTCCTGGAAC AAAGTTCAAA AAGCCGAAAA CGGGAAGAAA ACTAACCACA    1200
AAAGTAAAGG AACCACTTAG CCTTCTTTGA TTCCAGGCCC CCAAGCCTGT CTTTAACTTG    1260
GATGAATGGA GTTCTTCCTG TGCTACAGCA CCGCATAGTA GGGGCTGCCC TGGGCCTGAA    1320
GCCAGAGCTT CACCATATTC AGTCATCTGT ACATTGAGGC AACAGTGCCT GCTTCATGGT    1380
GCTACCCTGT GGATTAAATG AAGCAAGTTT TTGATGATCT TGACACTGAA TATTGATGCA    1440
TTGGTCAGAC TTTTTCTGAT AGTAAAAAAT GGTGGTTTCT TGTTGTCAGA AATCAAATCA    1500
ATATATTTGT TCTCCTGTTG ATTAGCTATG TCCCCTAGAG GGCAGCGACT TTGCCTGTCT    1560
TATTTATCTC TGCATCTCCA GCACTTAAAA GGTGCCTTGC ATAAGGTACA TATTAAGTTC    1620
ATATGAATGA ATGAATGAAA TGCATATGAT TTATTCATAC CCAGTTGGTG GTGTGTTTAC    1680
CCTTTCCTAA ACCTGTAGTC AGATGGCCTT TGAATCCCCT GTACTTCTTG TGAGGTACTG    1740
TGCTGTAAAG GTGGACTATC ACACTTCAGT TCAGAGCAAT CTGGGCTTGA ATCCTGGATT    1800
TGCCAGTTTA TTAACTATAG CAAACATTTT TGAGCATACA TTGTGCCAAG TGCTAGGCTA    1860
ACTGTCTTAC ACACATTGTC TTATTTCGTC TTAATATCTA TGAGTCATGC ACTATAATCA    1920
TCCCCATTTT ACAGATAAGA AAGCAAAGAC TTGGAGAGGA AAAGCATCTT GTTCAAAGGT    1980
AAATACTTAA TGGCCAAGCC AACATGCAAA TCTAGATTTA ATTGCAGCTT CCTCTTCATC    2040
TACCATTCGA ACTAATTCAA GCTATGTAAT ATTTCCCACT GAACCTTCTT GCCTCTACTT    2100
CCTCATCTTT AACATGGTCA AAATACCTGT CCTGCCCAAG TTAGTTATTT CATTAAAGTA    2160
GAAAATACA AGAGAAGCTT TTAAAATGTG AAACCTCAAA TGAATGTAAA ATTATGATGA    2220
TTCCTTTAGA ATTTGTCAAC ACCTTCTTTT CTCTACTCCT GCTAGGCATT TACAATCTCA    2280
AAACCATGTA TTTAAGATGC AAAACTATAT TTGTATTTGC CATAACTGGT TTCTTTCCCT    2340
ATGGCTTCAT GAAAATGTGG CTCGAATGTG TTTATTATGA AAGCCCCAAA TTAATCACGA    2400
CAAGACTTCA CCAGCCCATT CCACAATAGA CTCCCATTAC TTTGCCCTGA CTTAGAAACC    2460
TCATATACAG TCTTGATTCA GTACAGCTCT GTGATGCTCT TGGAAAATGC AAAGTGCTTT    2520
CTTAATTGAG GCAATCTGTG TCCCACTACA GAGAGGTGGT TTAACTTGTG AATTC         2575
```

( 2 ) INFORMATION FOR SEQ ID NO:11:

( i ) SEQUENCE CHARACTERISTICS:
        ( A ) LENGTH: 2316 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

| | | | | | | |
|---|---|---|---|---|---|---|
| AGAGCAACCT | GGGCAACATA | GCAAAACCCT | GTCTCTGCAA | ACAATAAAAA | GAAGAAAATT | 60 |
| AGCTGGGTAT | GGTGGCACAT | GCTATAGTCG | CAGCTACTCG | AGAGGTTGAG | GTGGGAGGAT | 120 |
| CAGTTCAGCC | TGGGAGGTTG | AGGCTGCAGT | GAGCCAGATC | ATGCCACTGC | ACTGCAGCAT | 180 |
| GGGCAACAGA | ATGAGACCCT | GGCTAAAAGA | AAACAAAATA | AAAAATTCAG | ACACAGGTTG | 240 |
| AATCATTGAT | AACAGCATAG | TGGTAACAGA | AAGAAAGTTT | GGGAAATTTT | TATCTGATCA | 300 |
| GCTTCCCATA | CCCTGTTCAT | CTTTGTGTTA | TGCACTGCCA | GGCTGTCTGT | AGGTTCAGAC | 360 |
| TCTATATCAT | ATGACCTTCA | AACACTTGGT | TTGTTCTTCT | CCTTCCTTCC | TCCCTTCTTC | 420 |
| TTTCATTTTT | TATCTTTTTT | TCTTTTAAAA | TGTTTAGATA | GTATAATAAG | GAACTGCTGA | 480 |
| GGCTTTCCAG | TGCCTCCCTC | AACATCCGGA | CAGCTAAGGA | GGATTTCACT | TTGCACCTTG | 540 |
| AGGACGGTTC | CTACAACATC | CGAAAAGATG | ACATCATAGC | TCTTTACCCA | CAGTTAATGC | 600 |
| ACTTAGATCC | AGAAATCTAC | CCAGACCCTT | TGGTAAAGTC | GCAGTGTGCC | CGAATTGAAA | 660 |
| TTCAATATCC | AGGTGATAGC | TACCTAGATC | TAAATAAAGA | GGAAATTTAC | AATGGTAGAA | 720 |
| TTGATTTTCT | CATAGTAGTC | ACAGGAATTG | TCTGACTTAA | TTGTGTTAAA | TATTCATATA | 780 |
| TTTTGGAAAA | TTTAGATAGT | GGTCTGAATT | TTTCATTTTA | GTCCTGATAT | TTGCCATCAC | 840 |
| ACAGTCTTTG | CTAGATTATA | TTTGCAGTCA | TGATAATAAA | CCTGCCACTT | TTTTTTTCTT | 900 |
| AAAAAGCACC | TCCTCCCAAA | TCCAGGAAAT | TGGAGGCTAA | TATATTGATT | ATTCTAGTTT | 960 |
| CTTCTGGGAA | CCCTTCTCTC | TCTAGCTCTG | CCTGACTAAG | GAACTAATCG | TTCAAGCAGG | 1020 |
| ATAGGAAGGT | ATCACAAGGC | TTCCTTAGCT | GCATTAAGCT | CCTGTTCCTT | ATTACTTTCT | 1080 |
| GATTCAATGT | GGAGTATTTG | CTAAATCACT | AATGGGGTAG | AATTAAAAAG | AAAATTACTC | 1140 |
| TTTGGAGCTT | CCAGGTTTAG | AAAGAGATAA | ATTTCTTTAA | AACTAGCTTA | AAGGCGGTTT | 1200 |
| TCTTTGTATT | TTTATTGCAG | ACTTTTAAAT | ATGATAGGTA | TCTTGATGAA | AACGGGAAGA | 1260 |
| CAAAGACTAC | CTTCTATTGT | AATGGACTCA | AGTTAAAGTA | TTACTACATG | CCCTTTGGAT | 1320 |
| CGGGAGCTAC | AATATGTCCT | GGAAGATTGT | TCGCTATCCA | CGAAATCAAG | CAATTTTTGA | 1380 |
| TTCTGATGCT | TTCTTATTTT | GAATTGGAGC | TTATAGAGGG | CCAAGCTAAA | TGTCCACCTT | 1440 |
| TGGACCAGTC | CCGGGCAGGC | TTGGGCATTT | TGCCGCCATT | GAATGATATT | GAATTTAAAT | 1500 |
| ATAAATTCAA | GCATTTGTGA | ATACATGGCT | GGAATAAGAG | GACACTAGAT | ATTACAGGAC | 1560 |
| TGCAGAACAC | CCTCACCACA | CAGTCCCTTT | GGACAAATGC | ATTTAGTGGT | GGCACCACAC | 1620 |
| AGTCCCTTTG | GACAAATGCA | TTTAGTGGTG | GTAGAAATGA | TTCACCAGGT | CCAATGTTGT | 1680 |
| TCACCAGTGC | TTGCTTGTGA | AATCTTAACA | TTTTGGTGAC | AGTTTCCAGA | TGCTATCACA | 1740 |
| GACTCTGCTA | GTGAAAAGAA | CTAGTTTCTA | GGAGCACAAT | AATTTGTTTT | CATTTGTATA | 1800 |
| AGTCCATGAA | TGTTCATATA | GCCAGGGATT | GAAGTTTATT | ATTTTCAAAG | GAAAACACCT | 1860 |
| TTATTTTATT | TTTTTTCAAA | ATGAAGATAC | ACATTACAGC | CAGGTGTGGT | AGCAGGCACC | 1920 |
| TGTAGTCTTA | GCTACTCGAG | AGGCCAAAGA | AGGAGGATGC | TTGAGCCCAG | GAGTTCAAGA | 1980 |
| CCAGCCTGGA | CAGCTTAGTG | AGATCCCGTC | TCCAAAGAAA | AGATATGTAT | TCTAATTGGC | 2040 |
| AGATTGTTTT | TTCCTAAGGA | AACTGCTTTA | TTTTTATAAA | ACTGCCTGAC | AATTATGAAA | 2100 |
| AAATGTTCAA | ATTCACGTTC | TAGTGAAACT | GCATTATTTG | TTGACTAGAT | GGTGGGGTTC | 2160 |
| TTCGGGTGTG | ATCATATATC | ATAAAGGATA | TTTCAAATGT | TATGATTAGT | TATGTCTTTT | 2220 |
| AATAAAAAGG | AAATATTTTT | CAACTTCTTC | TATATCCAAA | ATTCAGGGCT | TTAAACATGA | 2280 |
| TTATCTTGAT | TTCCCAAAAA | CACTAAAGGT | GGTTTT | | | 2316 |